(12) United States Patent
Halazonetis et al.

(10) Patent No.: US 7,217,532 B2
(45) Date of Patent: May 15, 2007

(54) METHODS FOR DETECTING DNA DAMAGE AND SCREENING FOR CANCER THERAPEUTICS

(75) Inventors: Thanos Halazonetis, Wynnewood, PA (US); Linda B. Schultz, Suwanee, GA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 652 days.

(21) Appl. No.: 10/276,312

(22) PCT Filed: May 30, 2001

(86) PCT No.: PCT/US01/17471

§ 371 (c)(1),
(2), (4) Date: Jan. 17, 2003

(87) PCT Pub. No.: WO01/91629

PCT Pub. Date: Dec. 6, 2001

(65) Prior Publication Data

US 2004/0023235 A1    Feb. 5, 2004

Related U.S. Application Data

(60) Provisional application No. 60/208,716, filed on Jun. 1, 2000.

(51) Int. Cl.
   *G01N 33/567*    (2006.01)
(52) U.S. Cl. .................. 435/7.21; 530/350; 530/387.9; 530/388.85; 530/389.1; 530/387.1; 530/387.3; 530/391.3
(58) Field of Classification Search .............. 435/7.1, 435/7.8, 7.92; 436/501; 530/300, 350, 387.1, 530/391.3, 389.1, 388.2, 387.9, 388.85, 387.3
See application file for complete search history.

(56) References Cited

OTHER PUBLICATIONS

Rappold et al. (J. Cell Biol. Apr. 30, 2001; 153 (3): 613-20).*
Skolnick et al. (Trends in Biotechnology. 2000; 18 (1): 34-39).*
Wu et al. (J. Immunol. 2005; 174: 934-941).*
Tuteja et al. (Crit. Rev. Biochem. Mol. Biol. 2001; 36 (6): 261-290).*
DiTullio et al. (Nature Cell Biol. Dec. 2002; 4: 998-1002; provided with supplementary information and corrigendum).*
Jullien et al. (J. Cell Sci. 2002; 115: 71-79).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*

J.H. Petrini, "DNA Repair '99—The Mammalian Mre11-Rad50-Nbs1 Protein complex: Integration of Functions in the Cellular DNA-Damage Response", *Am J. Hum. Genet.*, 64:1264-1269 (Apr. 6, 1999).
S.J. Elledge, "Cell Cycle Checkpoints: Preventing an Identity Crisis", *Science*, 274:1664-1672 (Dec. 6, 1996).
M.P. Longhese et al., "DNA Damage Checkpoint in Budding Yeast", *EMBO J.*, 17(19):5525-5528 (Oct. 1, 1998).
T. Weinert, "DNA Damage Checkpoints Update: Getting Molecular", *Curr. Opin. Genet. Dev.*, 8:185-193 (Apr. 1998).
L. Hartwell, "Defects in a Cell Cycle Checkpoint May Be Responsible for the Genomic Instability of Cancer Cells", *Cell*, 71:543-546 (Nov. 13, 1992).
C. Lengauer et al., "Genetic Instabilities in Human Cancers", *Nature*, 396:643-649 (Dec. 17, 1998).
L.A. Loeb, "Mutator Phenotype May Be Required for Multistage Carcinogenesis", *Cancer Res.*, 51:3075-3079 (Jun. 15, 1991).
T. Bessho et al., "Human DNA Damage Checkpoint Protein hRAD9 is a 3' to 5' Exonuclease", *J. Biol. Chem.*, 275:7451-7454 (Mar. 17, 2000).
H.B. Lieberman et al., "A Human Homolog of the *Schizosaccharomyces pombe rad9+* Checkpoint Control Gene", *Proc. Natl. Acad. Sci. USA*, 93:13890-13895 (Nov. 1996).
R.P.ST. Onge et al., "The Human G2 Checkpoint Control Protein hRAD9 is a Nuclear Phosphoprotein that Forms complexes with hRAD1 and hHUS1", *Mol. Biol. Cell.*, 10:1985-1995 (Jun. 1999).
E. Volkmer et al., "Human Homologs of *Schizosaccharomyces pombe* Rad1, Hus1, and Rad9 Form a DNA Damage-Responsive Protein Complexes", *J. Biol. Chem.*, 274:567-570 (Jan. 8, 1999).
K. Savitsky et al., "A Single Ataxia Telangiectasia Gene with a Product Similar to PI-3 Kinase", *Science*, 268:1749-1753 (Jun. 23, 1995).
N.J. Bentley et al., "The *Schizosaccharomyces pombe rad 3* Checkpoint", *EMBO J.*, 15(23):6641-6651 (Dec. 2, 1996).
T.D. Halazonetis et al., "Many Faces of ATM: Eighth International Workshop on Ataxia-Telangiectasia", *Biochim. Biophys,. Acta*, 1424:R45-55 (Oct. 29, 1999).
K.A. Cimprich et al., "cDNA Cloning and Gene Mapping of a Candidate Human Cell Cycle Checkpoint Protein", *Proc. Natl. Acad. Sci. USA*, 93:2850-2855 (Apr. 1996).
A. Blasina et al., "A Human Homologue of the Checkpoint Kinase Cds1 Directly Inhibits Cdc25 Phosphatase", *Curr. Biol.*, 9:1-10 (Jan. 1999).

(Continued)

*Primary Examiner*—Stephen L. Rawlings
(74) *Attorney, Agent, or Firm*—Howson & Howson LLP

(57) ABSTRACT

A method for detecting DNA damage in a tissue sample involves contacting an immobilized biological sample with a labeled ligand which binds to human 53Bp1, and examining the immobilized sample for the presence of a label generated-detectable signal concentrated in foci in said sample. The presence of concentrated foci is indicative of DNA damage and the presence of diffuse signal is indicative of a normal sample. Diagnostic reagents contain a ligand that binds to human 53Bp1 associated with a detectable label. Diagnostic kits for detecting DNA damage in a biological sample contain such diagnostic reagents and signal detection components. Compositions that inhibit or antagonize the biological activity of 53Bp1 are identified by suitable assays, and are employed in methods of retarding the growth of a cancer cell.

6 Claims, 2 Drawing Sheets

OTHER PUBLICATIONS

A.L. Brown et al., "A Human Cds1-Related Kinase that Functions Downstream of ATM Protein in the Cellular Response to DNA Damage", *Proc. Natl. Acad. Sci. USA*, 96:3745-3750 (Mar. 1999).

S. Matsuoka et al., "Linkage of ATM to Cell Cycle Regulation by the Chk2 Protein Kinase", *Science*, 282:1893-1897 (Dec. 4, 1998).

N.H. Chehab et al., "Chk2/hCds1 Functions as a DNA Damage Checkpoint in $G_1$ by Stabilizing p53", *Genes Dev.*, 14:278-288 (Feb. 1, 2000).

D.W. Bell et al., "Heterozygous Germ Line hCHK2 Mutations in Li-Fraumeni Syndrome", *Science*, 286:2528-2531 (Dec. 24, 1999).

T. Weinert et al., "The *RAD9* Gene Controls the Cell Cycle Response to DNA Damage in *Saccharomyces cerevisiae*", *Science*, 241: 317-322 (Jul. 15, 1988).

P. Bork et al., "A Superfamily of Conserved Domains in DNA Damage-Responsive Cell Cycle Checkpoint Proteins", *FASEB. J.*, 11:68-76 (Jan. 1997).

I. Callebaut et al., "From BRCA1 to RAP1: A Widespread BRCT Module Closely Associated with DNA Repair", *FEBS Lett.*, 400:25-30 (Jan. 2, 1997).

A.G. Paulovich et al., "When Checkpoints Fail", *Cell*, 88:315-321 (Feb. 7, 1997).

Y. Sanchez et al., "Regulation of RAD53 by the *ATM*-Like Kinases *MEC1* and *TEL1* in Yeast Cell Cycle Checkpoint Pathways", *Science*, 271:357-360 (Jan. 19, 1996).

Z. Sun et al., "Spk1/Rad53 is Regulated by Mec1-Dependent Protein Phosphorylation in DNA Replication and Damage Checkpoint Pathways", *Genes Dev.*, 10:395-406 (Feb. 15, 1996).

R.S. Maser et al., "hMre11 and hRad50 Nuclear Foci are Induced During the Normal Cellular Response to DNA Double-Strand Breaks", *Mol. Cell. Biol.*, 17:6087-6096 (Oct. 1997).

B.E. Nelms et al., "In Situ Visualization of DNA Double-Strand Break Repair in Human Fibroblasts", *Science*, 280:590-592 (Apr. 24, 1998).

M. Löbrich et al., "Repair of X-Ray-Induced DNA Double-Strand Breaks in Specific *Not* I Restriction Fragments in Human Fibroblasts: Joining of Correct and Incorrect Ends", *Proc. Natl. Acad. Sci. USA*, 92:12050-12054 (Dec. 1995).

R. Scully et al., "Dynamic Changes of BRCA1 Subnuclear Location and Phosphorylation State are Initiated by DNA Damage", *Cell*, 90:425-435 (Aug. 8, 1997).

J.S. Lee et al., "hCds1-Mediated Phosphorylation of BRCA1 Regulates the DNA Damage Response", *Nature*, 404:201-204 (Mar. 9, 2000).

Y. Wang et al., "BASC, a Super Complex of BRCA1-Associated Proteins Involved in the Recognition and Repair of Aberrant DNA Structures", *Genes Dev.*, 14:927-939 (Apr. 15, 2000).

Q. Zhong et al., "Association of BRCA1 with the hRad50-hMre11-p95 complex and the DNA Damage Response", *Science*, 285:747-750 (Jul. 30, 1999).

T. Haaf et al., "Nuclear Foci of Mammalian Rad51 Recombination Protein in Somatic Cells After DNA Damage and its Localization in Synaptonemal Complexes", *Proc. Natl. Acad. Sci. USA*, 92:2298-2302 (Mar. 1995).

T.L. Tan et al., "Mouse Rad54 Affects DNA Conformation and DNA-Damage-Induced Rad51 Foci Formation", *Curr. Biol.*, 9(6):325-328 (Mar. 25, 1999).

C. Morrison et al., "The Controlling Role of ATM in Homologous Recombinational Repair of DNA Damage", *EMBO J.*, 19:463-471 (2000).

C. Morrison et al., "The Controlling Role of ATM in Homologous Recombinational Repair of DNA Damage", *EMBO J.*, 19(4):786 (2000).

V. Gharibyan et al., "Localization of the Bloom Syndrome Helicase to Punctate Nuclear Structures and the Nuclear Matrix and Regulation during the Cell Cycle: Comparison with the Werner's Syndrome Helicase", *Mol. Carcinog.*, 26:261-273 (Dec. 1999).

T. Lindahl et al., "Quality Control by DNA Repair", *Science*, 286:1897-1905 (Dec. 3, 1999).

K. Iwabuchi et al., "Two Cellular Proteins that Bind to Wild-Type but not Mutant p53", *Proc. Natl. Acad. Sci. USA*, 91:6098-6102 (Jun. 1994).

K. Iwabuchi et al., "Stimulation of p53-Mediated Transcriptional Activation by the p53-Binding Proteins", *J. Biol. Chem.*, 273:26061-26068 (Oct. 2, 1998).

Z. Xia et al., "Negative Cell Cycle Regulation and DNA Damage-Inducible Phosphorylation of the BRCT Protein 53BP1", *J. Biol. Chem.*, 276(4):2708-2718 (Jan. 26, 2001).

L. Anderson et al., "Phosphorylation and Rapid Relocalization of 53BP1 to Nuclear Foci Upon DNA Damage", *Mol. Cell. Biol.*, 21(5):1719-1729 (Mar. 2001).

L.B. Schultz et al., "p53 Binding Protein 1 (53BP1) is an Early Participant in the Cellular Response to DNA Double-Strand Breaks", *J. Cell. Biol.*, 151(17):1381-1390 (Dec. 25, 2000).

Gorgoulis et al., "*Activation of the DNA damage checkpoint and genomic instability in human precancerous lesions*", Nature, Apr. 14, 2005, vol. 434(7035): pp. 907-913.

* cited by examiner

METHODS FOR DETECTING DNA DAMAGE AND SCREENING FOR CANCER THERAPEUTICS

CROSS-REFERENCE TO RELATED APPLICATIONS

This is a national stage of PCT/US01/17471, filed May 30, 2001, which claims the benefit of the priority of U.S. Patent Application No. 60/208,716, filed Jun. 1, 2000.

This invention was supported, at least in part, by National Institute of Health, Grant No. 5RO1 CA76367-03. The United States government has certain rights in this invention.

FIELD OF THE INVENTION

The present invention relates to methods and compositions for diagnosis of cancer and other consequences of DNA damage in mammalian cells and tissues, and to methods of drug screening for anti-cancer compounds.

BACKGROUND OF THE INVENTION

The stability or integrity of the genomes of eukaryotes is the result of a complex interplay of functions at the center of which is regulation of DNA damage checkpoints and DNA repair [Petrini, J. H., 1999 *Amer. J. Hum. Genet.*, 64:1264–1269]. In eukaryotes, when the DNA is damaged, the cell must first sense that damage is present, then induce cell cycle arrest by activating an evolutionarily conserved DNA damage checkpoint. The checkpoint causes arrest of the cell cycle at the G1/S and G2/M boundaries and activation of DNA repair functions [Elledge, S. J., 1996 *Science*, 274:1664–1672; Longhese, M. P. et al, 1998 *EMBO J.*, 17:5525–5528; Weinert, T. 1998 *Curr. Opin. Genet. Dev.*, 8:185–193].

Different agents cause different types of DNA damage. Genomic instability, which is a hallmark of neoplastic transformation, may result from defects in the cell cycle checkpoint proteins or DNA repair proteins [Hartwell, L. 1992 *Cell* 71:543–546; Lengauer, C. et al., 1998 *Nature*, 396:643–649; and Loeb, L. A., 1991 *Cancer Res.*, 51:3075–3079]. One of the most serious threats to genetic integrity is DNA double-strand breaks (DNA DSBs) which are produced from exogenous agents, such as ionizing radiation, and from errors occurring during normal replication or recombination. DNA DSBs are the most important agents of DNA damage from the cell's perspective, because they are the most difficult to repair.

Considerable information about DNA repair genes and DNA damage checkpoint genes is available. For example, checkpoint proteins are highly conserved and homologues of most are present in *S. pombe* and higher eukaryotes. Human homologues of *S. cerevisiae* RAD24, RAD17, MEC3 and DDC1 have been cloned and partially characterized [Bessho, T., and Sancar, A. 2000 *J. Biol. Chem.*, 275: 7451–7454; Lieberman, H. B. et al, 1996 *Proc. Natl. Acad. Sci. USA*, 93:13890–13895; St. Onge, R. P. M. et al, 1999 *Mol. Biol. Cell*, 10:1985–1995; Volkmer, E., and Karnitz, L. M. 1999 *J. Biol. Chem.*, 274: 567–570]. There are two putative human homologues of Mec1, ATM (ataxia-telangiectasia mutated) [Savitsky, K. et al, 1995 *Science*, 268: 1749–1753] and ATR (AT and rad-related) [Bentley, N. J. et al, 1996 *EMBO J.*, 15:6641–665 1]. In humans, ATM responds to DNA double stranded breaks (DSBs) and when inactivated in patients with ataxia telangiectasia leads to checkpoint defects in G1, S, and G2 [Halazonetis, T. D., and Shiloh, Y. 1999 *Biochim Biophys Acta*, 1424:R45–55]. Human ATR may mediate the response to DNA damage other than DSBs [Bentley (1996) cited above; Cimprich, K. A. et al, 1996 *Proc. Natl. Acad. Sci. USA*, 93:2850–2855]. Chk2, the human homologue of *S. cerevisiae* Rad53, becomes phosphorylated in response to DNA DSBs in an ATM-dependent manner [Blasina, A. et al, 1999 *Curr. Biol.*, 9:1–10; Brown, A. L. et al, 1999 *Proc. Natl. Acad. Sci. USA*, 96:3745–3750; Matsuoka, S. et al, 1998 *Science*, 282: 1893–1897] leading to stabilization of the tumor suppressor protein p53 and cell cycle arrest in G1 [Chehab, N. H. et al, 2000 *Genes Dev.*, 14:278–288; Matsuoka (1998) cited above]. Germ line mutations in Chk2 are found in Li-Fraumeni syndrome, a highly penetrant familial cancer phenotype typically associated with mutations in p53, suggesting that Chk2 is a tumor suppressor gene and when mutated leads to a predisposition to sarcoma, breast cancer, and brain [Bell, D. W. et al, 1999 *Science*, 286:2528–2531].

One of the few human homologues that remain to be found is that of budding yeast *S. cerevisiae* Rad9, which was the first checkpoint protein to be identified [Weinert, T. A., and Hartwell, L. H. 1988 *Science*, 241:317–322]. Rad9 is a component of the DNA damage checkpoint and is required for cell cycle arrest following genomic insult. Rad9 has two carboxy terminal BRCT (3RCA1 C terminus) domains which are found in many proteins with functions related to the DNA damage response, such as, BRCA1, NBS, XRCC4, DNA ligase 4, PARP, and many others [Bork, P. et al, 1997 *Faseb J.*, 11:68–76; Callebaut, I., and Mornon, J. P. 1997 *FEBS_Lett*, 400:25–30]. Rad9, along with proteins encoded by genes in the RAD24 epistasis group, including RAD17, RAD24, MEC3, and DDC1 [Longhese (1998), cited above; Paulovich, A. G. et al, 1997 *Cell*, 88:315–321; Weinert (1998) cited above] are proposed to sense DNA damage and regulate activation and phosphorylation of Mec1, a protein kinase required for subsequent phosphorylation and activation of Rad53/Spk1 and Chk1 kinases. Rad53/Spk1 and Chk1 then phosphorylate proteins that regulate progression through the cell cycle [Sanchez, Y. et al, 1996 *Science*, 271:357–360; and Sun, Z. et al, 1996 *Genes Dev.*, 10: 395–406].

However, very little is known about the proteins that actually sense DNA damage. The sensing protein varies depending on the type of DNA damage. For example, different proteins are required for activating the DNA damage checkpoint when the cell is exposed to UV light (which induces pyrimidine dimers) than the proteins that are required to activate the DNA damage checkpoint when the cell is exposed to ionizing radiation (which induces DNA strand breaks). Part of the difficulty in identifying sensor proteins is the inability to observe and/or isolate sites of DNA damage, such as DNA DSBs.

Proteins that localize to sites of DNA damage are involved in DNA repair and/or checkpoint control. Thus, one approach useful for visualizing DSBs is by immunofluorescence using antibodies to proteins known to localize to such sites. Such an approach has been employed with the Mre11/Rad50/NBS protein complex, which is involved in DNA repair and checkpoint functions. The Mre11/Rad50/NBS complex forms nuclear foci in response to ionizing radiation that localize to sites of DNA DSBs between four and eight hours after irradiation. Approximately 50% of cells contain on average 12 Mre11 foci per cell 8 hours following 12 Gy gamma irradiation [Maser, R. S. et al, 1997 *Mol. Cell. Biol.*, 17: 6087–6096]. Petrini (1999), cited above exposed partially shielded cells to synchrotron generated ultrasoft x-rays followed by immunofluorescence to probe for Mre11. Mre11 relocalized to the non-shielded areas in a striped pattern corresponding to the regions exposed to X-rays [Nelms, B. E. et al., 1998 Science, 280:590–592]. However, DNA breaks occur immediately after X-rays or gamma irradiation and most of them are repaired well before the four hour time point in which Mre11 foci are evident [Lobrich, M. et al, 1995 Proc. Natl. Acad. Sci. USA, 92:12050–12054]. Also, limited accessibility to a synchrotron irradiator does not allow this approach for visualizing DSB's to be used routinely.

Other proteins that localize to points of DNA damage include BRCA1 [Scully, R. et al, 1997 Cell, 90: 425–435] and Chk2 [Lee, J. S. et al, 2000 Nature, 404:201–204]. BRCA1 and Chk2 form foci predominately in S-phase cells in the absence of DNA damage. These foci disperse within one hour of gamma irradiation and reform approximately 8 hours later [Lee (2000), cited above]. Approximately 10% of cells contain BRCA1 foci that colocalize with the Mre11/Rad50/NBS complex at sites of DNA DSBs [Wang, Y. et al, 2000 Genes Dev., 14:927–939; Zhong, Q. et al, 1999 Science, 285:747–750].

Still other proteins that have been reported to form nuclear foci or redistribute in the nucleus in response to DNA damage are Rad51 [Haaf, T. et al, 1995 Proc. Natl. Acad. Sci. USA, 92:2298–2302] and Rad54 [Tan, T. L. et al, 1999 Curr. Biol., 9:325–328]. Rad51 and Rad54 form nuclear foci in response to ionizing radiation. The foci increase in number with time following treatment with irradiation [Morrison, C. et al, 2000 EMBO J, 19:463–471 and 19(4):786]. Yet another such protein is BLM, which localizes to punctate nuclear structures normally [Gharibyan, V., and Youssoufian, H. 1999 Mol. Carcinog., 26:261–273].

Still other proteins known to localize to sites of DNA DSBs, such as the DNA-PK/Ku complex, ATM and ATR, DNA ligase 4, XRCC4 and PARP, do not form visible nuclear foci in response to DNA damage using immunofluorescence [Lindahl, T., and Wood, R. D. 1999 Science, 286:1897–1905].

Thus, there is at present no method which can use these proteins for the observation and/or isolation of DNA DSBs.

The human p53-binding protein, 53Bp1 was identified in a yeast two-hybrid assay as a protein that binds the p53 tumor suppressor protein. The 53Bp1 was found to bind to the central DNA binding domain of wildtype, but not mutant, p53 and to enhance p53-mediated transcriptional activation of p21. 53Bp1 was proposed to have a role as a transactivator of p53 [Iwabuchi, K. et al, 1994 Proc. Natl. Acad. Sci. USA, 91:6098–6102; Iwabuchi, K. et al, 1998 J. Biol. Chem., 273:26061–26068]. Although 53Bp1 shares no overall homology to other known proteins, the carboxy terminus contains two tandem BRCT domains which are sufficient for binding to p53 [Iwabuchi (1998), cited above]. The nucleotide and protein sequences of 53Bp1 are provided in GENBANK database Accession No. AF078776, submitted Jul. 16, 1998.

There remains a need in the art for methods and compositions for identifying cells and tissues which have sites of DNA damage, e.g., tumor cells, for diagnostic purposes as well as for screening methods for the identification of useful cancer therapeutics.

SUMMARY OF THE INVENTION

In one aspect, the present invention provides a method for detecting DNA damage in a tissue sample. This method involves contacting a biological sample with a ligand which binds to human 53Bp1. The ligand is associated with a label which provides a detectable signal. When the sample, preferably immobilized, is examined for the presence of signal, the signal is either in concentrated foci of 53Bp1 in the sample or diffused throughout the sample. The presence of concentrated foci is indicative of DNA damage and the presence of diffuse signal is indicative of a normal sample.

In another aspect, the invention provides a diagnostic reagent comprising a ligand that binds to human 53Bp1, the ligand associated with a detectable label.

In still a further aspect, the invention provides a diagnostic kit for detecting DNA damage in a biological sample. The kit comprises a diagnostic reagent which is a ligand which binds to human 53Bp1, the ligand associated with a detectable label, and suitable components for detection of the label.

In another aspect, the invention provides a method of screening test compounds to identify a composition that inhibits or antagonizes the biological activity of 53Bp1, such as a small chemical compound, or inhibits the expression of 53Bp1, such as an antisense sequence. The method comprises employing a 53Bp1 ligand associated with a detectable label to detect the expression of 53Bp1 in a cell contacted with a test compound or to detect the presence or number of 53Bp1 induced nuclear foci in cells contacted with a test compound.

In yet another aspect of the invention, a composition which antagonizes or inhibits the biological activity or expression of 53Bp1 is provided, which composition is optionally identified by the above method.

In still another aspect of the invention, there is provided a method of retarding the growth of a cancer cell, the method comprising administering to the site of a cancer cell a 53Bp1 inhibitor that prevents the 53Bp1 from performing its DNA repair function or inhibits the expression of 53Bp1.

In yet a further aspect of the invention, there is provided a method of targeting a tumor cell for delivery of a therapeutic agent, comprising administering to a patient bearing a tumor containing 53Bp1 foci a ligand that binds to 53Bp1, said ligand associated with a compound that retards the growth of, or kills, the tumor cell.

Other aspects and advantages of the present invention are described further in the following detailed description of the preferred embodiments thereof.

DETAILED DESCRIPTION OF THE INVENTION

Figure 1A:
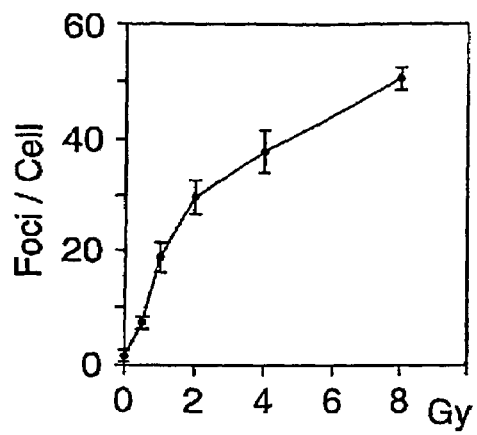
FIG. 1A is a graph demonstrating the mean number and standard deviation of 53Bp1 foci per cell one hour after exposure to ionizing radiation as a function of the dose of radiation exposure in Gy.

The present invention provides novel methods for detecting DNA damage in a cell or tissue, as well as novel diagnostic reagents, and methods and compositions for screening for anti-cancer drugs and treating cancer, based on the human p53-binding protein, hereinafter referred to as 53Bp1.

A. Characteristics of 53Bp1

Using the genomes of *C. elegans* and *Drosophila,* the inventors characterized 53Bp1 as having a function quite distinct from the function that has been identified for 53Bp1 by the prior art, i.e., as a transactivator of p53. The inventors have identified that 53Bp1 is a DNA damage responsive protein that functions upstream of ATM and is a homologue of budding yeast Rad9 based on the degree of protein similarity between these two proteins. 53Bp1 contains BRCT domains at amino acid residues 1713 to 1973 of SEQ ID NO: 2. Although proteins containing BRCT domains have diverse functions, their common involvement in the cellular response to DNA damage and the link between 53Bp1 and p53 suggest a potential similar role for 53Bp1. The inventors have determined, as evidenced in the examples below, that 53Bp1 functions early in the DNA repair pathway. 53Bp1 localizes early to DNA DSBs in a time and dose-dependent manner which is ATM-independent and then colocalizes with the Mre11/Rad50/NBS-p95 complex. These data indicate that 53Bp1 participates in the cellular responses to DNA damage and functions as a DNA checkpoint or repair protein and, therefore, participate in the maintenance of genome integrity. This protein localizes to sites of DNA breaks earlier than other known proteins, and thus is useful in methods for readily and easily visualizing the presence of DNA breaks as evidence of DNA damage in cells. Additionally, as demonstrated below, concentrated foci of 53Bp1 are detectable in several genetically unstable tumor cell lines, thereby enabling this protein to be a useful target for development and identification of novel cancer therapeutic agents, and possibly the delivery of other therapeutic agents.

By the term "biological activity of 53Bp1" as used herein, is meant the ability to localize quickly to DNA DSBs, as well as to localize in discrete foci in certain tumor cells. The other characteristics of 53Bp1, identified by the inventors, are discussed throughout this specification and included in this definition. See, Examples 1 through 7, that demonstrate other characteristics of the 53Bp1 protein.

The known encoding nucleic acid sequence (SEQ ID NO: 1) and protein sequence (SEQ ID NO: 2) of human 53Bp1 are provided in GENBANK database Accession No. AF078776, submitted Jul. 16, 1998. As used herein, the term "53Bp1 nucleic acid sequence" refers not only to the isolated nucleic acid segment or fragment reported in SEQ ID NO: 1, which has been separated from sequences which flank it in a naturally occurring state, e.g., a DNA fragment which has been removed from the sequences which are normally adjacent to the fragment, such as the sequences adjacent to the fragment in a genome in which it naturally occurs. The term also applies to nucleic acids which have been substantially purified from other components which naturally accompany the nucleic acid, e.g., RNA or DNA or proteins, in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic fragment produced by PCR or restriction enzyme digestion) independent of other sequences. It also includes a recombinant DNA which is part of a hybrid gene encoding additional polypeptide sequence.

When used in the compositions and methods of this invention, the term 53Bp1 can include fragments of the protein (or of nucleotide sequences encoding the protein). Such fragments may include fragments that are minimally necessary for targeting the 53Bp1 to the site of DNA damage. As taught in Example 9, one such fragment may be that comprising amino acid residues 1220 to 1711 of SEQ ID NO: 2. Another fragment is a deletion mutant which is missing an unnecessary portion of the 53Bp1 sequence. For example, one such deletion mutant fragment spans amino acid residues 1 to 1711 of SEQ ID NO: 2, or is a fusion of AA residues 1–1053 with 1220–1972, or AA residues 1–34 with AA residues 1047–1972, or AA residues 1–34 with AA residues 1047–1711, or AA residues 1–34 with AA residues 1220–1711 of SEQ ID NO: 2. Still other fragments of 53Bp1 which contain only necessary targeting sequences, e.g., more than the minimal sequence AA 1220 to 1711 of SEQ ID NO: 2 can be designed and used by one of skill in the art given the teachings herein.

When used in the compositions and methods of this invention, the isolated nucleic acid of 53Bp1, or fragments of that sequence encoding minimal targeting fragments of 53Bp1, should not be construed as being limited solely to the known nucleotide sequences of SEQ ID NO: 1, but rather should be construed to include any and all nucleotide sequences which share homology (i.e., have sequence identity) with that nucleotide sequence. Preferably, the invention includes an isolated nucleic acid having a nucleotide sequence which is at least 70% identical to the nucleotide sequence presented in SEQ ID NO: 1. More preferably, an isolated nucleic acid of this invention has a nucleotide sequence which is at least 75% identical, even more preferably, 80% identical, yet more preferably, 85% identical, and even more preferably, 90% identical to the nucleotide sequence presented in SEQ ID NO: 1. Even more preferably, an isolated nucleic acid of this invention has a nucleotide sequence which is at least 95% identical, and most preferably, 99% identical, to the nucleotide sequence presented in SEQ ID NO: 1. Any such isolated nucleic acid would of course encode a polypeptide having the biological activity of 53Bp1, as disclosed herein.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGGC 5' share 50% homology. As used herein, "homology" is used synonymously with "identity".

Percent identity, percent similarity or percent homology of one polynucleotide or polypeptide with respect to another identified polynucleotide or polypeptide is calculated using algorithms, such as the Smith-Waterman algorithm [J. F. Collins et al, 1988, Comput. Appl. Biosci., 4:67–72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp. 417], and the BLAST program and FASTA programs [E. G. Shpaer et al, 1996, Genomics, 38:179–191]. A preferred algorithm is the computer program BLAST, especially blastp or tblastn (Altschul et al., 1997). These references are incorporated herein by reference. Sequence homology for polypeptides, which is also referred to as sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as the GAP program and BESTFIT program, which can be used with default parameters to determine sequence homology or sequence identity between closely related polypeptides, such as homologous polypeptides from different species of organisms or between a wild type protein and a mutein thereof. Unless otherwise specified, the parameters of each algorithm discussed above are the default parameters identified by the authors of such algorithms.

Among such homologous nucleotide sequences of this invention are allelic variants of the 53Bp1 sequence of SEQ ID NO: 1 within a species (i.e., sequences containing some individual nucleotide differences from a more commonly occurring sequence within a species, but which nevertheless encode the same polypeptide or a protein with the same function). Additionally nucleic acid sequences capable of hybridizing under stringent conditions [see, J. Sambrook et al, Molecular Cloning: A Laboratory Manual, 2d ed., Cold Spring Harbor Laboratory (1989)] to the sequences of SEQ ID NO: 1, their anti-sense strands, or biologically active fragments thereof are homologous sequences according to this invention. An example of a highly stringent hybridization condition is hybridization at 2×SSC at 65° C., followed by a washing in 0.1×SSC at 65° C. for an hour. Alternatively, an exemplary highly stringent hybridization condition is in 50% formamide, 4×SSC at 42° C. Moderately high stringency conditions also prove useful, e.g., hybridization in 4×SSC at 55° C., followed by washing in 0.1×SSC at 37° C. for an hour. An alternative exemplary moderately high stringency hybridization condition is in 50% formamide, 4×SSC at 30° C.

Depending upon its use in the methods and compositions of this invention, the known 53Bp1 nucleic acid sequence [SEQ ID NO: 1] is modified. Utilizing the known sequence, useful modifications are within the skill of the art, e.g., synthetic or recombinant polynucleotide sequences, or modified polynucleotide sequences, encoding the full-length 53Bp1 protein or useful fragments thereof. Such modifications at the nucleic acid level include, for example, modifications to the nucleotide sequences which are silent or which change the amino acids, e.g. to improve expression or secretion. Also included are allelic variations, caused by the natural degeneracy of the genetic code. Additional homologous sequences can include mutants including 5' or 3' terminal or internal deletions, which truncated or deletion mutant sequence are expressed for the purpose of affecting the activity of the full-length or wild-type 53Bp1 polypeptide or fragments.

Similarly, the term 53Bp1 protein or polypeptide, or fragments encompassing the minimal targeting fragment, as used herein should not be construed as being limited solely to the known amino acid sequence of SEQ ID NO: 2, but rather should be construed to include any and all amino acid sequences which share homology (i.e., have sequence identity) with those amino acid sequences. Preferably, the methods and compositions of this invention make use of a polypeptide having an amino acid sequence which is 70% identical, more preferably, 75% identical, even more preferably, 80% identical, yet more preferably, 85% identical, even more preferably, 90% identical, more preferably, 95% identical and most preferably, 99% or 100% identical to the known amino acid sequence presented in SEQ ID NO: 2. Reference to 53Bp1 herein includes the definitions of "homologous", "homology" and "percent identity" as discussed above, including the list of computer algorithms available to calculate these homologies. Any such preparation of a homologous polypeptide has the biological activity of the 53Bp1 as disclosed herein.

Also included in the invention are modified versions of the 53Bp1 polypeptide. Typically, such polypeptides differ from the known 53Bp1 polypeptide of SEQ ID NO: 2 by only one to four codon changes. Examples include polypeptides with minor amino acid variations from the known amino acid sequence of 53Bp1 (SEQ ID NO: 2), in particular, conservative amino acid replacements. Conservative replacements are those that take place within a family of amino acids that are related in their side chains and chemical properties. Further encompassed by this invention are compositions and methods employing fragments of 53Bp1, including fragments containing the minimal targeting sequences identified above. Useful fragments are designed or obtained in any desired length, including as small as about 5–8 amino acids in length, or larger fragments, such as about 490 amino acids or more. Such fragments are desirably characterized by localizing to the sites of DNA DSBs or having a biological activity similar to the intact 53Bp1.

B. Methods of Preparing Sequences of this Invention

Methods for obtaining the nucleic acids and polypeptides of the invention should be apparent to those skilled in the art given the present disclosure and the instructions known to one of skill in the art. For example, the nucleotide and polypeptide sequences useful in the compositions and methods of the invention are prepared conventionally by resort to known chemical synthesis techniques, e.g., solid-phase chemical synthesis, such as described by Merrifield, 1963 *J. Amer. Chem. Soc.,* 85:2149–2154, and J. Stuart and J. Young, Solid Phase Peptide Synthelia, Pierce Chemical Company, Rockford, Ill. (1984), or detailed in the examples below.

Alternatively, the nucleotide and polypeptide sequences useful in the methods and compositions of this invention are prepared by known recombinant DNA techniques and genetic engineering techniques, such as polymerase chain reaction, by cloning and expressing within a host microorganism or cell a DNA fragment carrying a nucleic acid sequence encoding the above-described polypeptides, etc. [See, e.g., Sambrook et al., Molecular Cloning. A Laboratory Manual., 2d Edit., Cold Spring Harbor Laboratory, New York (1989); Ausubel et al. (1997), Current Protocols in Molecular Biology, John Wiley & Sons, New York]. The 53Bp1 are obtained from gene banks derived from whole genomic DNA. These sequences, fragments thereof, modifications thereto and the full-length sequences are constructed recombinantly using conventional molecular biology techniques, site-directed mutagenesis, genetic engineering or PCR, and the like by utilizing the information provided herein. For example, methods for producing the above-identified modifications of the sequences, include mutagenesis of certain nucleotides and/or insertion or deletion of nucleotides, or codons, thereby effecting the polypeptide sequence by insertion or deletion of, e.g., non-natural amino acids, are known and selected by one of skill in the art.

1. Expression In Vitro

To produce recombinant 53Bp1 or other fragments of this invention in vitro, the DNA sequences of the invention are inserted into a suitable expression system. Desirably, a recombinant molecule or vector is constructed in which the polynucleotide sequence encoding the selected protein is operably linked to a heterologous expression control sequence permitting expression of the protein. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known. See, Sambrook et al, cited above; Miller et al, 1986 *Genetic Engineering*, 8:277–298 and references cited therein.

Suitable host cells or cell lines for transfection by this method include bacterial cells. For example, the various strains of *E. coli* (e.g., HB101, MC1061, and strains used in the following examples) are well-known as host cells in the field of biotechnology. Various strains of *B. subtilis, Pseudomonas, Streptomyces*, and other bacilli and the like are also employed in this method. Mammalian cells, such as human 293 cells, Chinese hamster ovary cells (CHO), the monkey COS-1 cell line or murine 3T3 cells derived from Swiss, Balb-c or NIH mice are used. Another suitable mammalian cell line is the CV-1 cell line. Still other suitable mammalian host cells, as well as methods for transfection, culture, amplification, screening, production, and purification are known in the art. [See, e.g., Gething and Sambrook, 1981 *Nature*, 293:620–625, or alternatively, Kaufman et al, 1985 *Mol. Cell. Biol.*, 5(7):1750–1759 or Howley et al, U.S. Pat. No. 4,419,446]. Many strains of yeast cells known to those skilled in the art are also available as host cells for expression of the polypeptides of the present invention. Other fungal cells are also be employed as expression systems. Alternatively, insect cells such as *Spodoptera frugipedera* (Sf9) cells may be used.

Thus, the present invention provides a method for producing a recombinant 53Bp1 protein, which involves transfecting, e.g., by conventional means such as electroporation, a host cell with at least one expression vector containing a polynucleotide of the invention under the control of a transcriptional regulatory sequence. The transfected or transformed host cell is then cultured under conditions that allow expression of the protein. The expressed protein is recovered, isolated, and optionally purified from the cell (or from the culture medium, if expressed extracellularly) by appropriate means known to one of skill in the art. For example, the proteins are isolated in soluble form following cell lysis, or extracted using known techniques, e.g., in guanidine chloride. If desired, the proteins or fragments of the invention are produced as a fusion protein to enhance expression of the protein in a selected host cell, to improve purification, or for use in monitoring the presence of the desired protein in tissues, cells or cell extracts. Suitable fusion partners for the proteins of the invention are well known to those of skill in the art and include, among others, β-galactosidase, glutathione-S-transferase, and poly-histidine.

2. Expression In Vivo

Alternatively, where it is desired that the 53Bp1 protein or ligand useful in the methods and compositions of the invention or proteinaceous inhibitors thereof (whether full-length or a desirable fragment) be expressed in vivo, e.g., to induce antibodies, or as a therapeutic, an appropriate vector for delivery is readily selected by one of skill in the art. Exemplary vectors for in vivo gene delivery are readily available from a variety of academic and commercial sources, and include, e.g., adeno-associated virus [International patent application No. PCT/US91/03440], adenovirus vectors [M. Kay et al, 1994 *Proc. Natl. Acad. Sci. USA*, 91:2353; S. Ishibashi et al, 1993 *J. Clin. Invest.*, 92:883], or other viral vectors, e.g., various poxviruses, vaccinia, etc. Methods for insertion of a desired gene, e.g., P7–1, and obtaining in vivo expression of the encoded protein, are well known to those of skill in the art.

The preparation or synthesis of the nucleotide and polypeptide sequences, including the ligands disclosed herein, whether in vitro or in vivo (including ex vivo) is well within the ability of the person having ordinary skill in the art using available material. The synthetic methods are not a limitation of this invention.

C. Ligands and Inhibitors of 53Bp1

Based on the information on the biological activities of 53Bp1 identified by the inventors, the present invention provides in one aspect, compositions that can inhibit the expression of the protein and hence prevent its biological function, as well as compositions that bind to the protein and antagonize, inhibit or block the biological functions of 53Bp1.

Such compositions have utility as diagnostic reagents or as therapeutic reagents in the methods described below. By the use of the term "53Bp1 ligand or 53Bp1 protein ligand" as used herein is meant a compound, e.g., an antibody, which is capable of detecting the formation of concentrated 53Bp1 nuclear foci in cells exposed to agents which cause DNA DSBs by binding to some characteristic portion or epitope of 53Bp1. Such ligands are additionally characterized as antagonizing or inhibiting the biological function of 53Bp1. By the term "53Bp1 inhibitor" is meant a composition which inhibits or prevents the expression of 53Bp1, such as an antisense sequence which binds to the 53Bp1 messenger RNA, and thereby inhibits or prevents the biological function of 53Bp1. Inhibition of 53Bp1 activity by either a 53Bp1 ligand or a 53Bp1 inhibitor is assessed by following the procedures presented in the examples herein, which permit the formation of foci or lack of such formation to be detected.

1. Nucleotide Sequence 53Bp1 Inhibitors

One such 53Bp1 inhibitor is a nucleotide sequence that binds to the 53Bp1 nucleic acid sequence or a fragment thereof, preferably the 53Bp1 mRNA. For example, such a 53Bp1 inhibitor includes an oligonucleotide molecule which is preferably in an antisense orientation with respect to the nucleic acid sequence of 53Bp1. As used herein, the term "antisense oligonucleotide" means a nucleic acid polymer, at least a portion of which is complementary to a 53Bp1 mRNA or other nucleic acid, particularly the BRCT domains. "Antisense" refers particularly to the nucleic acid sequence of the noncoding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence is complementary to regulatory sequences specified on the coding strand of a DNA molecule encoding a protein, which regulatory sequences control expression of the coding sequences.

The antisense oligonucleotides of the invention preferably comprise between about fourteen and about fifty nucleotides. More preferably, the antisense oligonucleotides comprise between about twelve and about thirty nucleotides. Most preferably, the antisense oligonucleotides comprise between about sixteen and about twenty-one nucleotides. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art [U.S. Pat. No. 5,034,506; Nielsen et al., 1991, *Science* 254:1497].

By binding to the mRNA of 53Bp1, the antisense sequence inhibits expression of the 53Bp1 protein, and thereby prevents or inhibits the 53Bp1 biological DNA repair function.

2. Polypeptide/Protein Ligands

In another embodiment, another ligand composition of the invention binds to the 53Bp1 polypeptide. Such ligands, when contacted with a cell exposed to a DNA damaging agent which results in DNA DSBs, e.g., radiation, cancer, etc. can locate 53Bp1 foci in that cell. Such a ligand is desirably an antibody which binds to 53Bp1, e.g., the BRCT domains or other unique domains of 53Bp1. Preferably, such a ligand also inhibits 53Bp1 biological function. The term "antibody," as used herein, refers to an immunoglobulin molecule which is able to specifically bind to an epitope on 53Bp1, e.g., the BRCT domain. Antibodies can be intact immunoglobulins derived from natural sources or from recombinant sources and can be immunoreactive portions of intact immunoglobulins. Antibodies are typically tetramers of immunoglobulin molecules. The antibodies in the present invention exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE. One such desirable ligand is the anti-53Bp1 monoclonal antibody described in detail in Example 1. Other such antibodies include a Fab, Fab' or F(ab')2, or Fc antibody fragment thereof which binds 53Bp1. Still another useful ligand is a single chain Fv antibody fragment which binds 53Bp1.

Another useful ligand is a recombinant construct comprising a complementarity determining region of an antibody, a synthetic antibody or a chimeric antibody construct which shares sufficient CDRs to retain functionally equivalent binding characteristics of an antibody that binds 53Bp1. By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The antibodies of this invention are generated by conventional means utilizing the isolated, recombinant or modified 53Bp1 or fragments thereof as antigens of this invention. For example, polyclonal antibodies are generated by conventionally stimulating the immune system of a selected animal or human with a 53Bp1 antigen, allowing the immune system to produce natural antibodies thereto, and collecting these antibodies from the animal or human's blood or other biological fluid. Preferably a recombinant version of 53Bp1 is used as an immunogen. Monoclonal antibodies MAbs) directed against 53Bp1 are also generated conventionally. Hybridoma cell lines expressing desirable MAbs are generated by well-known conventional techniques, e.g. Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., 1986 *Science*, 233:747–753; Queen et al., 1989 *Proc. Nat'l. Acad. Sci. USA*, 86:10029–10033; PCT Patent Application No. PCT/WO9007861; and Riechmann et al., *Nature*, 332:323–327 (1988); Huse et al, 1988a *Science*, 246:1275–1281].

Given the disclosure contained herein, one of skill in the art generates ligands or antibodies directed against 53Bp1 by resort to known techniques by manipulating the complementarity determining regions of animals or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, *Proc. Natl. Acad. Sci. USA* 85:5879–5883; and Bird et al., 1988, *Science* 242:423–426.

Alternatively, 53Bp1 antigens are assembled as multi-antigenic complexes [see, e.g., European Patent Application 0339695, published Nov. 2, 1989] and employed to elicit high titer antibodies capable of binding the 53Bp1. Further provided by the present invention are anti-idiotype antibodies (Ab2) and anti-anti-idiotype antibodies (Ab3). Ab2 are specific for the target to which anti-53Bp1 antibodies of the invention bind and Ab3 are similar to 53Bp1 antibodies (Ab1) in their binding specificities and biological activities [see, e.g., M. Wettendorff et al., "Modulation of anti-tumor immunity by anti-idiotypic antibodies." In Idiotypic Network and Diseases, ed. by J. Cerny and J. Hiernaux, 1990 *J. Am. Soc. Microbiol., Washington D.C.: pp.* 203–229]. These anti-idiotype and anti-anti-idiotype antibodies are produced using techniques well known to those of skill in the art. Such anti-idiotype antibodies (Ab2) can bear the internal image of 53Bp1 and are thus useful for the same purposes as 53Bp1.

In general, polyclonal antisera, monoclonal antibodies and other antibodies which bind to 53Bp1 as the antigen (Ab1) are useful to identify epitopes of 53Bp1 to separate 53Bp1 and its analogs from contaminants in living tissue (e.g., in chromatographic columns and the like), and in general as research tools and as starting material essential for the development of other types of antibodies described above. Anti-idiotype antibodies (Ab2) are useful for binding the same target and thus are used in place of 53Bp1 to induce useful ligands to 53Bp1. The Ab3 antibodies are useful for the same reason the Ab1 are useful. Other uses as research tools and as components for separation of 53Bp1 from other contaminants, for example, are also contemplated for the above-described antibodies.

Other ligands include small chemical compounds that bind to 53Bp1 and prevents its ability to form nuclear foci. Still other chemical compounds bind to 53Bp1 and prevent its ability to participate in DNA repair. Such 53Bp1 ligands are identified and developed by the drug screening methods discussed in detail below.

3. Ligands/Inhibitors as Diagnostic Reagents and Kits

For use in diagnostic assays and kits for the detection of DNA DSBs caused by exposure to DNA damaging agents, the above-described inhibitors or ligands of 53Bp1 are preferably associated with a detectable label which is capable, alone or in concert with other compositions or compounds, of providing a detectable signal. Where more than one 53Bp1 inhibitor or ligand is employed in a diagnostic method, the labels are desirably interactive to produce a detectable signal. Most desirably, the label is detectable visually, e.g. by fluorescence, for ready use in immunohistochemical analyses or immunofluorescent microscopy. Preferably, each inhibitor or ligand is associated with, or conjugated to a fluorescent detectable fluorochromes, e.g., fluorescein isothiocyanate (FITC), phycoerythrin (PE), allophycocyanin (APC), coriphosphine-O (CPO) or tandem dyes, PE-cyanin-5 (PC5), and PE-TEXAS RED dye (ECD). All of these fluorescent dyes are commercially available, and their uses known to the art. Other useful labels include a colloidal gold label.

Still other useful labels include radioactive compounds or elements. Additionally, labels include a variety of enzyme systems that operate to reveal a calorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other label systems that are utilized in the methods of this invention are detectable by other means, e.g., colored latex microparticles [Bangs Laboratories, Indiana] in which a dye is embedded are used in place of enzymes to form conjugates with the inhibitor sequences or ligands and provide a visual signal indicative of the presence of the resulting complex in applicable assays.

Detectable labels for attachment to 53Bp1 inhibitors or ligands and antibodies useful in diagnostic assays of this invention are easily selected from among numerous compositions known and readily available to one skilled in the art of diagnostic assays. The diagnostic reagents, e.g., the inhibitors and ligands of this invention, are not limited by the particular detectable label or label system employed.

Methods for coupling or associating the label with the inhibitor or ligand are similarly conventional and known to those of skill in the art. Known methods of label attachment are described [see, for example, Handbook of Fluorescent probes and Research Chemicals, 6th Ed., R. P. M. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

For convenience, the conventional reagents for immunohistochemical analysis or immunofluorescent microscopy, or other diagnostic assays according to this invention are provided in the form of kits. Such kits are useful for determining and enumerating the absence or presence of 53Bp1 foci in a cell or tissue, particularly a tumor cell. Thus, such a kit will be useful in conducting the diagnostic assays discussed below, e.g., in determining if a cell is cancerous, in determining the status of cells or tissues exposed to DNA damage, etc. Such a diagnostic kit contains a nucleotide inhibitor (e.g., a 53Bp1 antisense sequence), or 53Bp1 ligand (e.g., an antibody capable of binding 53Bp1) of this invention. Alternatively, such kits contain a simple mixture of such inhibitors or means for preparing a simple mixture. The kits also include instructions for performing the assay, microscopic slides for fixing the tissue or cells, fixatives, suitable stains, or microtiter plates to which the inhibitors or nucleic acid sequences of the invention have been pre-adsorbed, various diluents and buffers, labeled conjugates for the detection of specifically bound compositions and other signal-generating reagents, such as fluorescent compounds and dyes, enzyme substrates, cofactors and chromogens. Other components include indicator charts for fluorescent or calorimetric comparisons, disposable gloves, decontamination instructions, applicator sticks or containers, and a sample preparator cup. Such kits provide a convenient, efficient way for a clinical laboratory to diagnose the presence or absence of DNA damage in a cell or tissue according to this invention.

4. Inhibitors/Ligands as Therapeutic Compositions of this Invention

Alternatively, an above-described inhibitor or ligand of 53Bp1 of this invention which antagonizes or inhibits the biological activity of 53Bp1, or which binds to the 53Bp1, is employed therapeutically, and as such, is encompassed in a pharmaceutical composition for treating cancers that are characterized by 53Bp1 nuclear foci. Such a composition includes a 53Bp1 ligand or inhibitor (nucleotide or polypeptide or protein) and a pharmaceutically-acceptable carrier. As used herein, the term "pharmaceutically-acceptable carrier" means a chemical composition with which an appropriate 53Bp1 inhibitor or ligand is combined and which, following the combination, is used to administer the appropriate 53Bp1 inhibitor or ligand to a mammal. Typical carriers include saline, buffered saline, and other inert compositions known and used in drug delivery. In addition to the appropriate 53Bp1 inhibitor or ligand, such pharmaceutical compositions optionally also contain other ingredients known to enhance and facilitate drug administration. Other possible formulations, such as nanoparticles, liposomes, resealed erythrocytes, and immunologically based systems are useful to administer an appropriate 53Bp1 inhibitor or ligand according to the methods of the invention.

Also, as noted herein, pharmaceutical compositions of this invention include a combination of compounds comprising a 53Bp1 ligand or inhibitor associated with another chemotherapeutic, which functions to kill or retard the growth of the cell containing 53Bp1 foci.

Still other compositions that inhibit 53Bp1 functions, such as compositions, synthetic compounds or other compounds identified as 53Bp1 ligands or inhibitors by the screening methods described below are optionally employed in pharmaceutical compositions for treating cancer.

Pharmaceutical therapeutic or vaccinal compositions that are useful in the methods of the invention are administered systemically in oral solid formulations, ophthalmic, suppository, aerosol, topical or other similar formulations which are administered intravenously, intraperitoneally, subcutaneously or by other routes known for pharmaceutical administration. Selection of the formulations and routes are within the skill of the art, and are not a limitation of this invention.

5. Research Uses for 53Bp1 Ligands

The above-described ligands are useful as research tools for categorizing tumor cells or other cancer cells which develop 53Bp1 foci in the absence of DNA damaging agents from normal cells or from cancer cells which develop such foci only after such exposure. Such ligands are useful in drug modeling in the methods disclosed below.

D. Diagnostic Methods of the Invention

Based on the novel biological activities of 53Bp1 as determined by the inventor, another embodiment of this invention is a method for simply and rapidly detecting DNA damage in a biological sample utilizing the above-mentioned ligands of 53Bp1. By "biological sample" is meant any mammalian cell or tissue, or cell or tissue-containing composition or isolate. For example, one biological sample may be a cell scraping, exudate or tissue specimen for biopsy, e.g., a buccal sample, sputum, cervical scraping. Another type of biological sample may be a preparation containing white blood cells, e.g., peripheral blood, sputum, saliva, urine, etc. for use in detecting the presence or absence of DNA damage in a patient that has been exposed to a DNA DSB inducing agent, such as radiation, chemicals, etc. Thus, the diagnostic method of this invention comprises contacting the biological sample, preferably immobilized or fixed on a surface, such as a microscope slide, with a ligand that binds to human 53Bp1. Such ligands are discussed in detail above, and are preferably associated with a label which provides a detectable signal, also as discussed above. The sample is then examined for the presence of signal concentrated in nuclear foci of 53Bp1 in the cells of the sample. The examining step is any suitable assay step, including, without limitation, fluorescent immunomicroscopy or immunohistochemical analysis.

The presence of concentrated foci is indicative of DNA damage, while the presence of diffuse signal is indicative of a lack of DNA damage in the sample. Thus, this method is used to rapidly and easily identify cancer cells in conventional cancer screening and is used to monitor the status of anti-cancer therapies. Additionally, this method is also employed to rapidly and readily assess the possibility of DNA damage in patients exposed to gamma irradiation or other DNA damage agents, particularly those known to cause DNA DSBs.

E. Drug Screening Methods of the Invention

Methods of screening test compounds are described which can identify a composition that either binds to 53Bp1, and is thus useful as a targeting agent for association with a chemotherapeutic agent, or a composition that binds to and inhibits or antagonizes the biological activity of 53Bp1 directly, and is thus useful as a direct chemotherapeutic. One such screening method can readily utilize the methods outlined in the examples below. For example, one method comprises employing a 53Bp1 ligand associated with a detectable label to detect the expression of 53Bp1 in a cell contacted with a test compound or to detect the presence or number of 53Bp1 induced nuclear foci in cells contacted with a test compound. Such a method involves contacting a selected cell with a test compound, and then exposing the selected cell and test compound (i.e., the "test cell") as well as an identical cell without test compound (i.e., the "control cell") to a DNA damaging agent, such as gamma irradiation. The test cell and control cell are then exposed to a 53Bp1 labeled ligand, such as a fluorescently-labeled anti-53Bp1. Because 53Bp1 nuclear foci form quickly after exposure of the cell to the damaging agent, the test cell and the control cell are then examined for the presence and number of 53Bp1 foci by a technique such as immunofluorescent microscopy. The results of such examination are then compared. The absence of foci in the test cell (or a significant reduction in the number of such foci) when compared to the control cell (which should have a significant number of foci) is an indication that the test compound inhibited the biological activity of 53Bp1 in this assay. The presence and/or number of foci is indicated by the level or intensity of the signal generated by the label on the ligand. The signal (or its level of expression or intensity) indicates the presence and number of 53Bp1 nuclear foci. When the signals generated by the label in the tests cell are compared with the signals (if any) generated by the labels in the control cell, a lesser detectable signal in the test cell indicates that said test compound has inhibited the presence and/or number of 53Bp1 foci in the cell (a) and is, in fact, a 53Bp1 inhibitor. Similar assays using different ligands, different detection techniques, etc. are readily designed by one of skill in the art with resort to the information provided in the art generally and in the examples below.

Inhibitors of 53Bp1 activity are screened by resort to assays and techniques useful in identifying drugs capable of binding to the 53Bp1 polypeptide and thereby inhibiting its biological activity in a cancer cell that expresses 53Bp1 in the absence of DNA damaging agents. Such assays include the use of phage display system for expressing the 53Bp1 polypeptide, and using a culture of transfected *E. coli* or other microorganism to produce the proteins for binding studies of potential binding compounds. See, for example, the techniques described in G. Cesarini, 1992 *FEBS Letters*, 307(1):66–70; H. Gram et al., 1993 *J. Immunol. Meth.*, 161:169–176; C. Summer et al., 1992 *Proc. Natl. Acad. Sci., USA*, 89:3756–3760, incorporated by reference herein.

Other conventional drug screening techniques are employed using the proteins, antibodies or polynucleotide sequences of this invention. As one example, a method for identifying compounds which specifically bind to a 53Bp1 polypeptide of this invention can include simply the steps of contacting a selected cell expressing 53Bp1 with a test compound to permit binding of the test compound to 53Bp1 and determining the amount of test compound, if any, which is bound to the 53Bp1. Such a method involves the incubation of the test compound and the 53Bp1 polypeptide immobilized on a solid support. Typically, the surface containing the immobilized ligand is permitted to come into contact with a solution containing the protein and binding is measured using an appropriate detection system. Suitable detection systems include those described above for diagnostic use.

Thus, through use of such methods, the present invention is anticipated to provide compounds capable of interacting with 53Bp1 or portions thereof, and either enhancing or decreasing 53Bp1's biological activity, as desired. Such compounds are believed to be encompassed by this invention.

Still other methods of drug screening for novel compounds that inhibit 53Bp1 expression at the nucleic acid or protein level involve computational evaluation and design.

According to these methods, the three dimensional structure of the 53Bp1 gene and/or the polypeptide is determined and chemical entities or fragments are screened and selected for their ability to associate with the three dimensional structures. Suitable software for such analysis include docking software such as QUANTA SOFTWARE and SYBYL software, molecular dynamics and mechanics programs, such as CHARMM and AMBER, the GRID program available from Oxford University, Oxford, UK. [P. J. Goodford, "A Computational Procedure for Determining Energetically Favorable Binding Sites on Biologically Important Macromolecules", 1985 *J. Med. Chem.*, 28:849–857]; the MCSS program available from Molecular Simulations, Burlington, Mass. [A. Miranker and M. Karplus, "Functionality Maps of Binding Sites: A Multiple Copy Simultaneous Search Method", 1991 *Proteins: Structure, Function and Genetics*, 11:29–34]; the AUTODOCK program available from Scripps Research Institute, La Jolla, Calif. [D. S. Goodsell and A. J. Olsen, "Automated Docking of Substrates to Proteins by Simulated Annealing", 1990 *Proteins: Structure, Function, and Genetics*, 8:195–202]; and the DOCK program available from University of California, San Francisco, Calif. [I. D. Kuntz et al, "A Geometric Approach to Macromolecule-Ligand Interactions", 1982 *J. Mol. Biol.*, 161: 269–288]. Additional commercially available computer databases for small molecular compounds include Cambridge Structural Database, Fine Chemical Database, and CONCORD database [for a review see Rusinko, A., *Chem. Des. Auto. News*, 8:44–47 (1993)].

Once suitable chemical entities or fragments have been selected, they can be assembled into a single compound or 53Bp1 inhibitor. Assembly may proceed by visual inspection of the relationship of the fragments to each other on the three-dimensional image displayed on a computer screen in relation to the 3D structure of 53Bp1. This would be followed by manual model building using software such as Quanta or Sybyl software, CAVEAT program [P. A. Bartlett et al, 1989 "CAVEAT: A Program to Facilitate the Structure-Derived Design of Biologically Active Molecules", in *Molecular Recognition in Chemical and Biological Problems*, Special Pub., *Royal Chem. Soc.* 78, pp. 182–196], which is available from the University of California, Berkeley, Calif.; 3D Database systems such as MACCS-3D database (MDL Information Systems, San Leandro, Calif.) [see, e.g., Y. C. Martin, "3D Database Searching in Drug Design", 1992 *J. Med Chem.*, 35:2145–2154]; and the HOOK program, available from Molecular Simulations, Burlington, Mass.

Other molecular modeling techniques are employed in accordance with this invention. See, e.g., N. C. Cohen et al, "Molecular Modeling Software and Methods for Medicinal Chemistry", 1990 *J. Med. Chem.*, 33:883–894. See also, M. A. Navia and M. A Murcko, "The Use of Structural Information in Drug Design", 1992 *Current Opinions in Structural Biology*, 2:202–21. For example, where the structures of test compounds are known, a model of the test compound is superimposed over the model of the structure of the invention. Numerous methods and techniques are known in the art for performing this step, any of which may be used. See, e.g., P. S. Farmer, Drug Design, Ariens, E. J., ed., Vol. 10, pp 119–143 (Academic Press, New York, 1980); U.S. Pat. Nos. 5,331,573; 5,500,807; C. Verlinde, 1994 *Structure*, 2:577–587; and I. D. Kuntz, 1992 *Science*, 257:1078–1082. The model building techniques and computer evaluation systems described herein are not a limitation on the present invention.

Thus, using these computer evaluation systems, a large number of compounds are quickly and easily examined and expensive and lengthy biochemical testing avoided. Moreover, the need for actual synthesis of many compounds is effectively eliminated. Once identified by the modeling techniques, the 53Bp1 inhibitors identified by these methods is tested for bioactivity using the assays described herein.

F. Pharmaceutical Methods of the Invention

As indicated by the examples below, certain cancer cells develop DNA DSBs and consequently 53Bp1 nuclear foci in the absence of known DNA damaging agents. Still other cells may become cancerous and develop such 53Bp1 foci only after exposure to DNA damaging agents. As another aspect, this invention provides a method for retarding the growth of or killing a cancer cell by administering to the site of a cancer cell a 53Bp1 inhibitor or ligand. Such an inhibitor antagonizes or inhibits the biological activity of the 53Bp1 directly and results in tumor cell death. In such a method, the administration of the inhibitor to the cell occurs ex vivo, e.g., for cells which are desired to be purged of cancer cells and returned to the patient, e.g., blood. Alternatively, the patient is treated in vivo by administering the ligand inhibitor in a suitable pharmaceutical preparation directly to a mammal having a cancer.

Still another pharmaceutical method involves using the 53Bp1 inhibitor to indirectly treat the tumor cell by binding to the 53Bp1 mRNA and inhibiting or preventing the expression of the protein. If the protein is inhibited, it cannot migrate to the site of DNA damage. The absence of the repair function of 53Bp1 makes the tumor cell more sensitive to damage by other, conventional chemotherapeutics, such as RicinA, toxins, bispecific antibodies associated with host protective cells, anticancer drugs, such as doxorubicin or 5-FU, optionally linked to another protein or ligand, among others.

In yet a further pharmaceutical regimen, the 53Bp1 ligand, such as a low affinity antibody or other ligand that preferentially binds to 53Bp1 foci, targets the tumor cell for delivery of another therapeutic agent, such as the agents identified above or other chemotherapeutic agents. In this method, the ligand is associated to a second compound that retards the growth of, or kills, the tumor cell, once it is delivered to the site of 53Bp1 foci by the binding of the ligand to the 53Bp1. The second compound includes, without limitation, a radionucleotide, a toxin, a bi-specific antibody and an anticancer drug optionally linked to a protein or peptide. The ligand with its associated chemotherapeutic compound, in a suitable pharmaceutical carrier, is delivered ex vivo or in vivo to the mammalian tissue. For example, the ligand is administered directly to a patient bearing tumor cells containing 53Bp1 foci or other cancer cells containing 53Bp1 foci.

These pharmaceutical compositions described above are administered via any suitable therapeutic route, and selection of such route is not a limitation of this invention. Similarly the appropriate dosage of such pharmaceutical compositions are determined by a physician, based on typical characteristics such as the physical condition of the patient, the disease being treated, the identity of the associated therapeutic or the subsequent or simultaneous uses of other therapeutic compositions, etc. In one embodiment, the pharmaceutical compositions useful for practicing the therapeutic methods of the invention are administered to deliver a dose of between 1 ng/kg/day and 100 mg/kg/day of the ligand. The dosage of the ligand is determined, adjusted and prepared for booster administrations, if any, by one of skill in the art. This invention is not limited by the dosage selection.

The following examples illustrate several embodiments of this invention. The following examples illustrate the function of 53Bp1 as a DNA damage-responsive protein in cycling cells, and demonstrate that 53Bp1 participates in the maintenance of genome integrity. These examples are illustrative only, and do not limit the scope of the present invention.

EXAMPLE 1

Experimental Procedures

A. Antibodies.

High affinity monoclonal antibodies, called anti-53BP1, were generated to be directed against the carboxy terminal BRCT domain of 53BP1. The monoclonal antibodies were generated by the conventional techniques described above, such as immunizing an animal using as the antigen a purified recombinant fragment of 53Bp1 encompassing the C-terminal 312 amino acids of 53Bp1 (amino acids 1662 to 1973 of SEQ ID NO: 2) which includes the BRCT domain (i.e., amino acids 1713 to 1973 of SEQ ID NO: 2). Other fragments of 53Bp1 are also used to make anti-53Bp1 antibodies by the published methods cited above. These antibodies were used in the examples below to probe the intracellular localization of 53Bp1.

Other antibodies used in the examples below are anti-Mre11 and p95/NBS, polyclonal antibodies (Calbiochem, San Diego, Calif.); anti Rad50, a polyclonal antibody (obtained from John Petrini at the University of Wisconsin); and Y11, a polyclonal antibody that recognizes the N-terminal hemaglutinin (HA) tags (Santa Cruz Biotech, Santa Cruz, Calif.).

B. Cell Lines.

Stably transfected U2OS cell lines were created by transfecting the plasmid pSV2 [Chehab, N. H. et al, 1999 Proc. Natl. Acad. Sci., USA, 96:13777–13782] containing various N-terminal hemaglutinin (HA) tagged versions of 53Bp1. HA53Bp1 is the full-length protein bearing the HA tag on its N terminus. HA53Bp1ΔBRCT is similar to HA53Bp1 with amino acids 1713 to 1973 (the BRCT domains) of SEQ ID NO: 2 deleted therefrom. HA53Bp1C312 contains only the C-terminal 312 amino acids of 53Bp1, which include the nuclear localization signal (i.e., amino acids 1662 to 1701 of SEQ ID NO: 2 and the BRCT domain (amino acids 1702–1973 of SEQ ID NO: 2). The U2OS cells on cover slips were transiently transfected with the selected plasmid using the calcium phosphate method. Positively transfected colonies were pooled after selecting with neomycin. Expression was allowed to occur for 30 hours and then cells were treated, fixed, stained, and visualized as described below.

C. Analysis of Ionizing Radiation-Induced Foci by Immunofluorescent Microscopy.

For use in the specifically defined experiments below, U20S cells grown on cover slips were mock treated for use as controls or the cells were exposed to DNA damaging agents, such as 50 J/m$^2$ UV light, 0.2 mM etoposide, 1 mM hydroxyurea, or between 0.5 and 12 Gy gamma irradiation via a $^{137}$Cs-irradiator. In some experiments, the cells were exposed to 20 μM of the fungal metabolite wortmannin, a known inhibitor of DNA-dependent protein kinase (DNA-PK) and double strand break rejoining, for 1 hour prior to irradiation. The wortmannin remained on cells for all time points. Five minutes to 24 hours later cells were fixed in 1% paraformaldehyde for 15 minutes, followed by extraction on ice for 20 minutes in 0.2% Triton X-100/phosphate buffered saline (PBS). Cover slips were incubated with the selected antibody for 1 hour at room temperature, washed with PBS and exposed to anti-mouse immunoglobulin (IgG) conjugated to the fluorescent dye, TEXAS RED (Vector Labs) or anti-rabbit IgG conjugated to fluorescein isothiocyanate (FITC) for 30 minutes at room temperature. After washing, the cells were counterstained with DAPI, washed, and mounted on glass slides. Slides were viewed with a Nihon fluorescent microscope using Q.E.D. software.

D. Coimmunoprecipitation Assays.

Nuclear extracts from mock treated U20S cells or cells exposed to 1 or 8 Gy gamma irradiation were prepared as described by Waterman et al, 1998 Nature Genet., 19:175–178. Endogenous 53BP1, Mre11, or p95/NBS were immunoprecipitated by binding 1 μg/reaction of monoclonal anti-53BP1, or 1 μg/reaction purified Mre11 or p95/NBS antisera (Calbiochem) in 1×IP buffer [25 mM Hepes (pH 7.4)/100 mM NaCl/5 mM MgCl$_2$/100 mM EDTA/0.2 mg/ml BSA/0.1% TWEEN-20surfactant] to protein-G SEPHAROSE beads (Amersham) for 1 hour. After washing three times with 1×IP buffer, 100 μg nuclear extract was added and proteins allowed to bind for 1 hour at 4° C. The beads were washed and the proteins resolved on 6% SDS-PAGE, transferred to PVDF membrane and were visualized by western blot using the antibodies described in Part A above.

EXAMPLE 2

53Bp1 Forms Nuclear Foci in Response to Ionizing Radiation

To investigate whether 53Bp1 participates in the cellular responses to DNA damage, the monoclonal antibodies of Example 1, Part A, directed against the carboxy terminus of 53Bp1 were used in an immunoblot analysis of whole cell extracts (WCE) from the transiently transfected U2OS cells ectopically expressing full length HA-tagged 53Bp1, HA53Bp1ΔBRCT, and HA53Bp1C312. These antibodies recognized specifically 53Bp1 as shown by immunoblot analysis, i.e., the antibodies bound to HA53Bp1 and HA53Bp1C312, but not HA53Bp1ΔBRCT.

Immunoblotting of endogenous 53Bp1 using nuclear extracts from cells either mock treated or exposed to 8 Gy ionizing radiation indicate that the steady state levels of 53Bp1 remain unchanged after gamma irradiation and that 53Bp1 is not detectably modified in response to DNA damage. Although the predicted molecular mass of 53Bp1 is approximately 217 kDa, the protein migrates significantly slower than its predicted size which is consistent with previous reports [Iwabuchi (1998) cited above].

Immunofluorescence experiments indicate that 53Bp1 is a uniformly distributed protein in the nuclei of unirradiated cells. However, following 8 Gy gamma irradiation, the subcellular distribution of 53Bp1 is altered to form distinct nuclear foci (i.e., ionizing radiation-induced foci or IRIF) in U20S cells. Nuclear foci formation is not limited to U20S cells, as 53Bp1 also relocalizes to foci in DLD1 and a variety of other normal cells under the same conditions (see below).

EXAMPLE 3

53Bp1 Localizes to Sites of DNA Double Stranded Breaks

To determine the type of DNA damage to which 53Bp1 was responding, cells were treated with either ionizing radiation, etoposide, hydroxyurea (HU), or ultraviolet (UV) irradiation and stained for 53Bp1, as described in Example 1.

53Bp1-containing foci are found specifically in cells exposed to ionizing radiation and etoposide, which cause DNA DSBs, and do not form in the nuclei of cells exposed to 50 J/m$^2$ UV light and stained 1–6 hours later, or in cells exposed to HU for 1 to 25 hours. These data show that 53Bp1 is relocalizing to DNA DSBs specifically.

In response to the agents that induce DNA double-strand breaks (DSBs), 53Bp1 localized at discrete foci within the nucleus of interphase cells. These foci appeared within 5 minutes after exposure to ionizing radiation.

EXAMPLE 4

53Bp1 Nuclear Foci Form in a Dose and Time Dependent Manner

Based on the response of 53Bp1 to ionizing radiation, experiments were performed to investigate whether this response was dose and time dependent. Ionizing radiation induces DNA DSBs at a linear rate of approximately 25 DSBs per human cell per Gy [rather than 36, as indicated by Lobrich (1995), cited above].

A. Dose Dependence

U2OS cells were exposed to 0.5, 1, 2, 4, and 8 Gy and these cells were stained one hour post-irradiation. The dose dependence of 53Bp1 foci formation in these cells was observed.

53Bp1-containing foci appeared after exposure of cells to 0.5 Gy and increased numbers were formed with increasing irradiation dose (see FIG. 1A). Moreover, the number of foci increase almost linearly with increasing irradiation dose and hence the number of DSB per cell.

B. Time Dependence

The time course for 53Bp1 foci formation following exposure to ionizing radiation was determined by exposing growing U2OS cells to 1 Gy of ionizing radiation and fixing the cells at 5, 15, 30, 45 and 60 minutes and 2, 4, 6, 8, 12, and 16 hours post-irradiation.

Figure 1B:
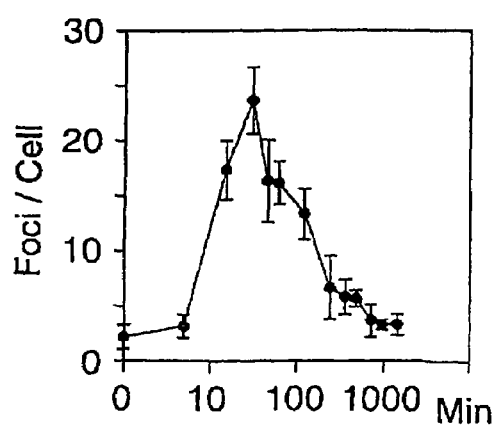
FIG. 1B is a graph showing the mean number and standard deviation of 53Bp1 foci per cell in cells exposed to 1 Gy ionizing radiation as a function of time in minutes after radiation exposure.
Figure 1C:
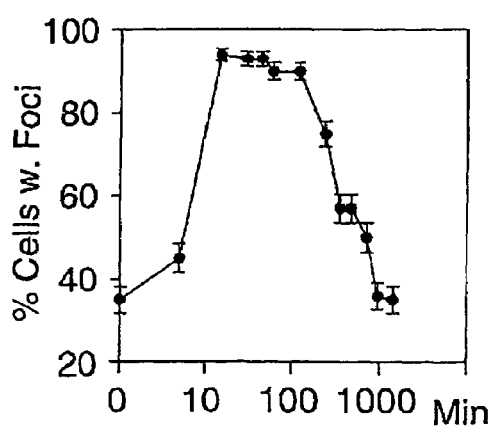
FIG. 1C is a graph showing the percentage of cells exhibiting 53Bp1 foci within a population of cells exposed to 1 Gy ionizing radiation as a function of time in minutes after radiation exposure.

Ionizing radiation-induced foci appeared within 15 minutes and greater than 90% of the nuclei contained 53Bp1 foci (see FIGS. 1B and 1C). The number of foci peak at 30 minutes and decrease to baseline values by 16 to 24 hours. These data are consistent with the hypothesis that 53Bp1 localizes to DNA DSBs and is removed when repair is complete.

In summary, the number of foci was proportional to the dose of ionizing radiation, peaked at the 30 minute time point and then decreased with biphasic kinetics that exhibited fast and slow components.

EXAMPLE 5

53Bp1 Colocalizes With, But Does Not Interact With, the MRE11/RAD50/NBS Complex The Mre11, Rad50 and NBS/p95 complex localizes to DNA DSBs in the form of ionizing radiation-induced foci [Maser (1997) and Nelms (1998), both cited above] which look similar to the 53Bp1-containing ionizing radiation-induced foci. Although 53Bp1-containing nuclear foci appear within 15 minutes of 1 Gy ionizing radiation, Mre11 and NBS foci appear four to eight hours post-irradiation and are visualized best following exposure to between 8 and 12 Gy.

A. 53Bp1 Colocalizes With the Mre11/Rad50/NBS/p95 Complex

To investigate further the site of 53Bp1 relocalization in the cellular response to DNA damage, an experiment was performed to determine whether 53Bp1 colocalizes with these proteins and with the promyelocytic leukemia protein (PML), another protein that forms nuclear foci as part of the nuclear domain 10 (ND10) structure [Ishov, A. M. et al, 1999 *J. Cell. Biol.*, 147:221–234], both in the absence and presence of DNA damage. U2OS cells were fixed 8 hours after exposure to 8 Gy irradiation and were stained with antibodies recognizing 53Bp1, Mre11, NBS and/or PML.

The 53Bp1 foci colocalize with Mre11 and NBS ionizing radiation-induced foci, i.e., with the Mre11/Rad50/NBS complex. There was no colocalization of 53Bp1 and the control protein, PML. These data indicate that the 53Bp1 and Mre11/NBS colocalization is specific.

B. 53Bp1 Does Not Interact With the Mre11/Rad50/NBS Complex

To determine if 53Bp1 was also part of this complex, a coprecipitation assay was performed as described in Example 1, Part D. Although Mre11, Rad50 and NBS could be co-immunoprecipitated under a variety of conditions, 53Bp1 never co-precipitated with this complex. These data do not support an interaction between these proteins under these conditions. However, these data do not preclude a functional interaction among the proteins as suggested by the colocalization data.

EXAMPLE 6

53Bp1 Foci Formation is Altered With Wortmannin Treatment

As an additional method to confirm that 53Bp1 plays a role in the DNA repair pathway, the transiently transfected U2OS cells of Example 1 were exposed to the fungal metabolite wortmannin and stained for 53Bp1 at various time points following 1 Gy ionizing radiation.

Figure 2A:
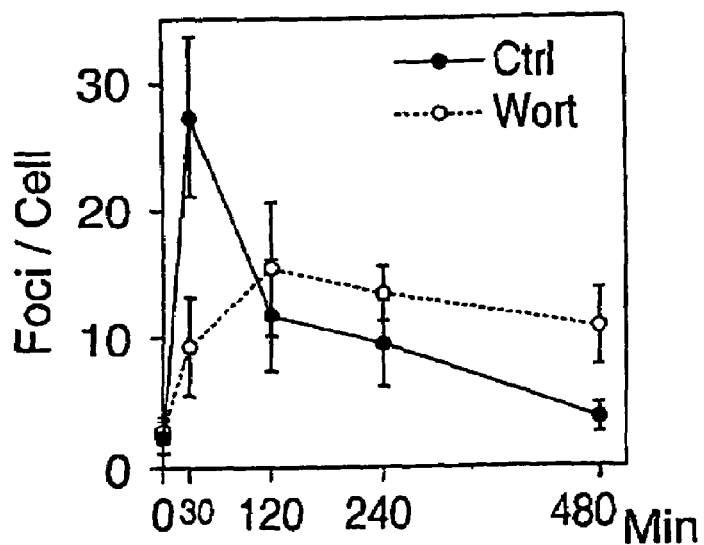
FIG. 2A is a graph demonstrating the effect of wortmannin on the kinetics of 53Bp1 foci/cell appearance and disappearance (i.e., the mean number and standard deviation) in cells exposed to 1 Gy ionizing radiation as a function of time in minutes after radiation exposure. Cells exposed to wortmannin (Wort, ●); control cells (Ctrl, ○).
Figure 2B:
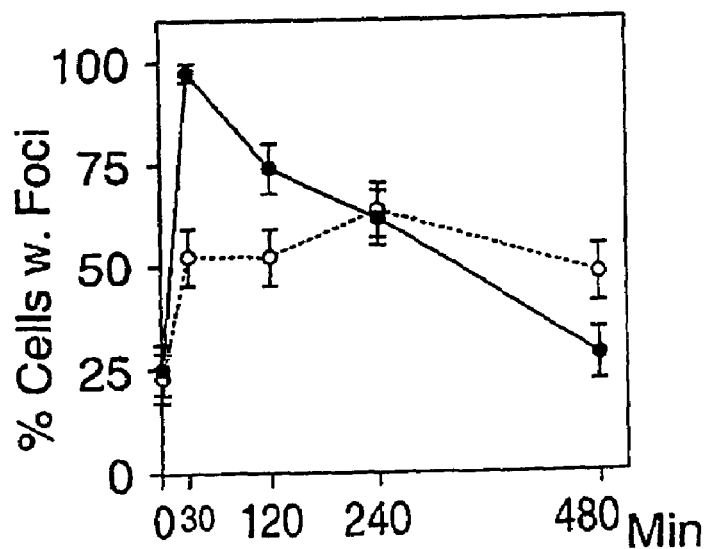
FIG. 2B is a graph demonstrating the effect of wortmannin on the percent of cells exhibiting 53Bp1 foci within a population of cells exposed to 1 Gy ionizing radiation as a function of time in minutes after radiation exposure. The symbols are identical to those of FIG. 2A.

Although 53Bp1 ionizing radiation-induced foci were present in some cells, the kinetics of foci formation were significantly altered. When compared to untreated controls, the wortmannin treated cells contained much lower numbers of foci at 30 minutes and the foci numbers did not decrease significantly over time (FIGS. 2A and 2B). Moreover, the percentage of cells containing 53Bp1 ionizing radiation-induced foci was reduced almost 50% at 30 minutes by the presence of wortmannin and then remained elevated over time relative to the control.

These data indicate that 53Bp1 localization is partially inhibited when DNA-PK, and hence DNA DSB repair, is inhibited by wortmannin. Wortmannin, which slows repair of DNA double-strand breaks (DSBs) slowed both the appearance and resolution of the 53Bp1 foci. These data provide further support that 53Bp1 plays a role in the response of cells to DNA damage.

In a similar study using caffeine rather than wortmannin, caffeine, which abrogates the DNA damage cell cycle checkpoint [Lau and Pardee 1982 *Proc. Natl. Acad. Sci., USA*, 79:2942–2946] did not affect 53Bp1 focus formation or dispersion in response to ionizing radiation. DNA-PK is theorized to be the kinase responsible for 53Bp1 relocalization because caffeine, which inhibits ATM and ATR, but not DNA-PK, did not affect 53Bp1 focus formation or dispersion.

EXAMPLE 7

53Bp1 Ionizing Radiation-Induced Foci Formation Does Not Require ATM or NIBRIN Because 53Bp1 participates in the cellular responses to DNA damage, this experiment investigated whether 53Bp1 foci formation was dependent on ATM or Nibrin (NBS/p95).

A. ATM Experiments

53Bp1 foci formation was examined in primary AT-1BR and AT-5BI cells which have mutations in the ATM gene and are derived from patients with ataxia telangiectasia. These AT mutated cells are deficient in their ability to signal the presence of DNA damage and are acutely sensitive to ionizing radiation. The ATM protein is activated following DNA damage as part of the DNA damage checkpoint. ATM is important for cell cycle arrest and appears to be needed for repair of chromosomal damage as well [Cornforth, M. N., and Bedford, J. S. 1985 *Science*, 227:1589–1591; Murnane, J. P. 1995 *Cancer Metastasis Rev.*,14:17–29 and 14(3): 253–4; Pandita, T. K., and Hittelman, W. N. 1992 *Radiat. Res.*, 130: 94–103].

The response in primary AT fibroblasts was compared to the normal counterpart cell line AG1522 after exposure to ionizing radiation. When exposed to 1 Gy of ionizing radiation and stained 15 minutes post-irradiation there was no significant difference in the cells' ability to form 53Bp1-containing nuclear foci when the AT mutated cells are compared to the AG1522 cells. These data indicate that relocalization of 53Bp1 in response to ionizing radiation can occur in the absence of ATM.

B. Nibrin Experiments

To determine if nibrin (NBS/p95) is required for formation of 53Bp1 ionizing radiation-induced foci, primary fibroblasts from patients with Nijmegen Breakage Syndrome were studied. The NBS cell lines 780816 and 880823 contain truncated versions of NBS and are radiosensitive, have radioresistant DNA synthesis and elevated levels of chromosomal aberrations [van der Burgt, I. et al, 1996 *J. Med. Genet.*, 33:153–156]. These NBS mutated cells were irradiated with 1 Gy, fixed, and stained with anti-53Bp1 15 minutes post-irradiation.

Many nuclear foci similar to those observed in irradiated U20S cells were observed in the NBS mutated cells, so treated. These data suggest that the formation of 53Bp1 ionizing radiation-induced foci does not require nibrin.

EXAMPLE 8

53Bp1 Ionizing Radiation-Induced Foci Are Present in Tumor Cell Lines in the Absence of Exogenous DNA Damage One cause of chromosomal instability, a hallmark of cancer cells, may stem from defects in DNA repair and DNA damage checkpoint genes leading to accumulations of DNA DSBs and increased chromosomal abnormalities. To monitor the presence of DNA DSBs, and to determine if there is an increased number of double stranded breaks in cancer cells, the tumor cell lines and normal primary cells identified specifically in Table 1 below, were incubated with the anti-53Bp1 antibody and examined by immunofluorescent microscopy as described in Example 1.

Table 1 provides an indication of whether such cell lines exhibit a low or high number of 53Bp1 foci in the absence of exposure to ionizing radiation. In the absence of exposure to DNA damaging agents, 53Bp1 foci were not evident in primary cells (normal fibroblast or osteoblast cells), but were evident in cancer cell lines. A high number of 53Bp1 foci were present in cells expected to have DNA damage lesions, such as MO59J, which lack DNA-PK, and HCC1937 cells, which lack functional BRCA1. The cancer cell lines SW480 and HCT11C also contained highly elevated numbers of 53Bp1 foci in the absence of DNA damage. Other tumor cell lines, also had a high number of 53Bp1 foci in the absence of exposure to DNA damaging agents.

TABLE 1

| | Number of 53Bp1 Foci |
|---|---|
| Tumor Cell Lines | |
| HCC1937 | Very High (>20 per cell) |
| HCT116 | High (>10 per cell) |
| SW480 | High (>10 per cell) |
| MO59J | High (>10 per cell) |
| HT29 | Low (~1 per cell) |
| MCF7 | Low (~1 per cell) |
| U2OS | Low (~1 per cell) |
| Normal Primary Cells | |
| Normal Dermal Fibroblasts | Low (<1 per cell) |
| Normal Osteoblasts | Low (<1 per cell) |

These data suggest that many tumor cells contain DNA DSBs in the absence of exogenous DNA damaging agents. As expected, the number of 53Bp1 foci were elevated in cells defective for the DNA repair proteins BRCA1 and DNA-PK (HCC1937 and M059J, respectively) without exposure to DNA damaging agents. This is further indication that it is DNA DSBs to which 53Bp1 is localizing. The fact that 53Bp1 foci were observed in some cancer cells, but not in primary cells, suggests that these cancer cell lines contain DNA DSBs, which may be the cause of chromosomal instability so common in tumors. These data suggest that creating molecules that block 53Bp1 provides a novel cancer therapeutic agent.

EXAMPLE 9

Mapping the Region of 53Bp1 That is Required for Its Ability to Form Ionizing Radiation/Induced Foci The following experiments were performed to identify the minimal focus-targeting (FT) domain of the relatively large (1972 amino acids) 53Bp1 protein [SEQ ID NO: 2]. The FT domain is the portion of the protein sequence required for targeting to ionizing radiation-induced foci. The FT domain participates in the mechanism of 53Bp1 relocalization. In addition, fragments of 53Bp1 that retain the ability to form ionizing radiation-induced foci act as dominant negative mutants by competing with endogenous 53Bp1 for localization to the IR-induced 53Bp1-binding sites.

There are two identifiable structural motifs in 53Bp1: a nuclear localization signal (NLS) between amino acids residues 1668–1685 of SEQ ID NO: 2 and two BRCT domains between amino acid residues 1724–1964 of SEQ ID NO: 2. The rest of the protein shows no obvious homology to any other protein.

A series of 53Bp1 deletion mutants was generated and expressed as HA-tagged proteins in U2OS cells. These cells were examined by immuno-fluorescence for their intracellular localization in response to ionizing radiation, as described in Examples 1 and 2. Nuclear localization is considered to be a prerequisite for targeting of 53Bp1 to ionizing radiation-induced foci. Therefore, all the mutants were constructed so that they retained the NLS of 53Bp1.

The results of this analysis are reported in Table 2 and show that three quarters of the 53Bp1 sequence, including the BRCT domains, are dispensable for relocalization in response to ionizing radiation. Specifically, amino acid residues 1220–1711 of SEQ ID NO: 2 are sufficient for the ability of 53Bp1 to form ionizing radiation-induced foci.

TABLE 2

| 53Bp1 Protein/Fragment | Ionizing Radiation-Induced Foci Localization |
| --- | --- |
| full-length (AA residues 1–1972 SEQ ID NO: 2) | Yes |
| AA residues 1–1711 (deletion of AA residues 1712–1972) of SEQ ID NO: 2 | Yes |
| AA residues 1661–1972 (deletion of residues 1–1660) of SEQ ID NO: 2 | No |
| AA residues 1–1053 and 1220–1972 (deletion of residues 1054–1219) of SEQ ID NO: 2 | Yes |
| AA residues 1–1053 and 1411–1972 (deletion of residues 1054–1410) of SEQ ID NO: 2 | No |
| AA residues 1–34 and 1047–1972 (deletion of residues 35–1046) of SEQ ID NO: 2 | Yes |
| AA residues 1–34 and 1047–1711 (deletion of residues 35–1046 and 1712–1972) of SEQ ID NO: 2 | Yes |
| AA residues 1–34 and 1220–1711 (deletion of residues 35–1219 and 1712–1972) of SEQ ID NO: 2 | Yes |
| AA residues 1–34 and 1411–1711 (deletion of residues 35–1410 and 1712–1972) of SEQ ID NO: 2 | No |

As demonstrated by the above Examples 1–8, within five minutes of cellular exposure to DNA DSB-inducing agents, 53Bp1 relocalizes from a homogenous nuclear distribution to very distinct nuclear foci at sites of DNA DSBs. First, 53Bp1 ionizing radiation-induced foci are seen when cells are treated with agents that induce DNA DSBs including gamma irradiation and etoposide. The ionizing radiation-induced foci are not present when cells are treated with HU, causing a replication block, or UV light, which causes the formation of pyrimidine dimers. Secondly, there is a distinct correlation between the number of 53Bp1 foci formed per Gy and the number of DNA DSBs per Gy. This suggests that the number of 53Bp1 foci approximate the number of DNA DSBs. Additionally, the kinetics of DNA DSB repair correlates with the kinetics of resolution of 53Bp1 ionizing radiation-induced foci over time. Thirdly, 53Bp1 ionizing radiation-induced foci colocalize with Mre11 and NBS ionizing radiation-induced foci which have been shown to localize to DNA DSBs. Lastly, the rate of 53Bp1 ionizing radiation-induced foci formation is significantly altered by wortmannin, a drug known to decrease the rate of DNA repair by inhibiting DNA-PK [Boulton, S. et al, 1996 Carcinogenesis, 17:2285–2290]. Taken together, these data provide strong evidence that 53Bp1 relocalizes to sites of DNA DSBs and remains localized until repair is complete.

Although other known proteins, identified above in the background section, either form nuclear foci or redistribute the foci in response to DNA damaging agents, none respond to DNA breaks by relocalizing to form foci within 5 minutes similar to 53Bp1. Moreover, the number of foci per cell is not proportional to the number of DNA DSBs and the fraction of cells containing foci for many of the proteins is low relative to the data for 53Bp1.

53Bp1 is part of the DNA damage checkpoint or repair pathways. 53Bp1 relocalizes to DNA DSBs even in cells that lack ATM, NBS, or BRCA1. These data indicate that these proteins are not required for the relocalization of 53Bp1 following irradiation. However, the rate of relocalization is likely affected. At five minutes post-irradiation, cells contain an increased number of foci, although the number of foci peak between 15 and 30 minutes. The fast, although not immediate, response implies that 53Bp1 is not the earliest cellular response after DNA damage. The DNA damage checkpoint kinase, ATM, is activated within two to five minutes [Banin, S. et al, 1998 Science, 281:1674–1677]. Ku is known to bind DNA ends quickly followed by recruitment of DNA-PK [Smith, G. C., and Jackson, S. P. 1999 Genes Dev., 13:916–934]. However, the time course of 53Bp1 ionizing radiation-induced foci localization implies an active process of recruitment of 53Bp1 to the site of DNA DSBs. The active recruitment of 53Bp1 is also supported by the data that wortmannin inhibits this recruitment.

53Bp1 has homology to the budding yeast Rad9, which is required for activation of the DNA damage checkpoint and is now proposed to participate in DNA repair through the NHEJ pathway [de la Torre-Ruiz, M., and Lowndes, N. F. 2000 FEBS Lett., 467:311–315; Weinert and Hartwell, 1988]. It is theorized that 53Bp1 has a similar role in mammalian cells. Because 53Bp1 responds early to DNA damage, it is likely a sensor protein which is necessary for proper signaling in either the checkpoint or repair pathways. ATM is activated within minutes following exposure to DNA double strand break agents. While the peak of 53Bp1 foci occurs at 15–30 minutes after DNA damage, foci are detected within five minutes of ionizing radiation. Thus, the initial response of 53Bp1 is fast enough to be consistent with 53Bp1 being part of the ATM-Chk2 DNA damage checkpoint pathway. Alternatively, or in addition, 53Bp1 is part of the NHEJ pathway as suggested by the colocalization with Mre11/Rad50/NBS. The fact that wortmannin, an inhibitor of PI-3-like kinases, decreases the rate of 53Bp1 recruitment to sites of DNA breaks suggests that DNA-PK or ATM is involved. 53Bp1 functions in the DNA damage checkpoint or repair pathway.

53Bp1 binds to the p53 DNA binding domain and not the transactivation domain, as a transactivator would. No p53 was detected coimmunoprecipitating with 53Bp1, however this does not preclude their potential interaction in vivo since p53 also colocalizes with 53Bp1 and it may not be possible to extract 53Bp1/p53 complexes from these foci.

Taken together, these data of Examples 1–9 indicate that 53Bp1 localizes to sites of DNA breaks earlier than other detectable proteins and colocalizes with other proteins that function in DNA repair and the DNA damage checkpoint. The recruitment of 53Bp1 to sites of DNA damage supports a role in DNA DSB processing and/or DNA damage signaling. In support of a role in DNA damage signaling, 53Bp1 has the highest similarity of all human sequences in the public databases to the C. elegans T05F1 open reading frame, which in turn is the C. elegans sequence with the highest similarity to the S. cerevisiae Rad9p and S. pombe Crb2p/Rhp9p sequences. Recruitment of 53Bp1 to sites of DNA damage represents an important step for DNA repair and/or DNA damage checkpoint control.

The documents and publications cited above are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for detecting DNA double strand breaks in cells, comprising the steps of:

contacting cells that have been exposed to ionizing radiation with an antibody or antibody fragment which specifically binds to human 53Bp1 protein, said protein consisting of the amino acid sequence of SEQ ID NO: 2, said antibody or fragment associated with a label which provides a detectable signal; and examining said cells for the presence of said signal concentrated in foci of said 53bp1 protein in said cells, wherein the presence of concentrated foci is indicative of DNA double strand breaks.

2. The method according to claim 1, further comprising immobilizing said cells prior to said contacting or examining steps.

3. The method according to claim 1 wherein said cells are white blood cells.

4. The method according to claim 1 wherein said cells are in a biopsy specimen.

5. The method according to claim 1 wherein said antibody or antibody fragment is selected from the group consisting of a polyclonal antibody, a monoclonal antibody of classes IgG, IgM, IgA, IgD and IgE, a recombinant antibody of classes IgG, IgM, IgA, IgD and IgE, an a Fab antibody fragment, a Fab' antibody fragment and a F(ab')2 antibody fragment.

6. The method according to claim 1, wherein said examining step comprises performing immunofluorescent microscopy or immunohistochemical analysis.

* * * * *

```
                              SEQUENCE LISTING

<160> NUMBER OF SEQ ID NOS: 2
<210> SEQ ID NO 1
<211> LENGTH: 6266
<212> TYPE: DNA
<213> ORGANISM: human 53Bp1
<220> FEATURE:
<221> NAME/KEY: CDS
<222> LOCATION: (174)..(6089)

<400> SEQUENCE: 1
cgttgtttgg cgtgtttttt tttttgtttt ttgtcactgc ctgcctgggt cctgcccgag      60
gtctccatcc tcggtttccc tgtccttgcc ccgggccctg ggagtgctct ggaaggctgc     120
gcagtattgg aggggacaga atgaccttcc ggccttgagt ccctggggag cag atg        176
                                                           Met
                                                            1 gac cct act gga agt cag ttg gat tca gat ttc tct cag caa gat act       224
Asp Pro Thr Gly Ser Gln Leu Asp Ser Asp Phe Ser Gln Gln Asp Thr
            5                  10                  15 cct tgc ctg ata att gaa gat tct cag cct gaa agc cag gtt cta gag       272
Pro Cys Leu Ile Ile Glu Asp Ser Gln Pro Glu Ser Gln Val Leu Glu
         20                  25                  30 gat gat tct ggt tct cac ttc agt atg cta tct cga cac ctt cct aat       320
Asp Asp Ser Gly Ser His Phe Ser Met Leu Ser Arg His Leu Pro Asn
     35                  40                  45 ctc cag acg cac aaa gaa aat cct gtg ttg gat gtt gtg tcc aat cct       368
Leu Gln Thr His Lys Glu Asn Pro Val Leu Asp Val Val Ser Asn Pro
 50                  55                  60                  65 gaa caa aca gct gga gaa gaa cga gga gac ggt aat agt ggg ttc aat       416
Glu Gln Thr Ala Gly Glu Glu Arg Gly Asp Gly Asn Ser Gly Phe Asn
                 70                  75                  80 gaa cat ttg aaa gaa aac aag gtt gca gac cct gtg gat tct tct aac       464
Glu His Leu Lys Glu Asn Lys Val Ala Asp Pro Val Asp Ser Ser Asn
             85                  90                  95 ttg gac aca tgt ggt tcc atc agt cag gtc att gag cag tta cct cag       512
Leu Asp Thr Cys Gly Ser Ile Ser Gln Val Ile Glu Gln Leu Pro Gln
        100                 105                 110 cca aac agg aca agc agt gtt ctg gga atg tca gtg gaa tct gct cct       560
Pro Asn Arg Thr Ser Ser Val Leu Gly Met Ser Val Glu Ser Ala Pro
    115                 120                 125 gct gtg gag gaa gag aag gga gaa gag ttg gaa cag aag gag aaa gag       608
Ala Val Glu Glu Glu Lys Gly Glu Glu Leu Glu Gln Lys Glu Lys Glu
130                 135                 140                 145 aag gaa gaa gat act tca ggc aat act aca cat tcc ctt ggt gct gaa       656
Lys Glu Glu Asp Thr Ser Gly Asn Thr Thr His Ser Leu Gly Ala Glu
                150                 155                 160 gat act gcc tca tca cag ttg ggt ttt ggg gtt ctg gaa ctc tcc cag       704
Asp Thr Ala Ser Ser Gln Leu Gly Phe Gly Val Leu Glu Leu Ser Gln
            165                 170                 175 agc cag gat gtt gag gaa aat act gtg cca tat gaa gtg gac aaa gag       752
Ser Gln Asp Val Glu Glu Asn Thr Val Pro Tyr Glu Val Asp Lys Glu
        180                 185                 190 cag cta caa tca gta acc acc aac tct ggt tat acc agg ctg tct gat       800
```

|     |     |     |     |     |     |     |     |     |     |     |     |     |     |      |
|---|---|---|---|---|---|---|---|---|---|---|---|---|---|---|
| Gln | Leu | Gln | Ser | Val | Thr | Thr | Asn | Ser | Gly | Tyr | Thr | Arg | Leu | Ser Asp |
|     | 195 |     |     |     | 200 |     |     |     |     | 205 |     |     |     |      |

| gtg | gat | gct | aat | act | gca | att | aag | cat | gaa | gaa | cag | tcc | aac | gaa | gat | 848 |
|---|---|---|---|---|---|---|---|---|---|---|---|---|---|---|---|---|
| Val | Asp | Ala | Asn | Thr | Ala | Ile | Lys | His | Glu | Glu | Gln | Ser | Asn | Glu | Asp |  |
| 210 |  |  |  |  | 215 |  |  |  |  | 220 |  |  |  |  | 225 |  |

| atc | ccc | ata | gca | gaa | cag | tcc | agc | aag | gac | atc | cct | gtg | aca | gca | cag | 896 |
|---|---|---|---|---|---|---|---|---|---|---|---|---|---|---|---|---|
| Ile | Pro | Ile | Ala | Glu | Gln | Ser | Ser | Lys | Asp | Ile | Pro | Val | Thr | Ala | Gln |  |
|  |  |  |  |  | 230 |  |  |  |  | 235 |  |  |  |  | 240 |  |

| ccc | agt | aag | gat | gta | cat | gtt | gta | aaa | gag | caa | aat | cca | cca | cct | gca | 944 |
|---|---|---|---|---|---|---|---|---|---|---|---|---|---|---|---|---|
| Pro | Ser | Lys | Asp | Val | His | Val | Val | Lys | Glu | Gln | Asn | Pro | Pro | Pro | Ala |  |
|  |  |  |  | 245 |  |  |  |  | 250 |  |  |  |  | 255 |  |  |

| agg | tca | gag | gac | atg | cct | ttt | agc | ccc | aaa | gca | tct | gtt | gct | gct | atg | 992 |
|---|---|---|---|---|---|---|---|---|---|---|---|---|---|---|---|---|
| Arg | Ser | Glu | Asp | Met | Pro | Phe | Ser | Pro | Lys | Ala | Ser | Val | Ala | Ala | Met |  |
|  |  |  | 260 |  |  |  |  | 265 |  |  |  |  | 270 |  |  |  |

| gaa | gca | aaa | gaa | cag | ttg | tct | gca | caa | gaa | ctt | atg | gaa | agt | gga | ctg | 1040 |
|---|---|---|---|---|---|---|---|---|---|---|---|---|---|---|---|---|
| Glu | Ala | Lys | Glu | Gln | Leu | Ser | Ala | Gln | Glu | Leu | Met | Glu | Ser | Gly | Leu |  |
|  | 275 |  |  |  |  | 280 |  |  |  |  | 285 |  |  |  |  |  |

| cag | att | cag | aag | tca | cca | gag | cct | gag | gtt | ttg | tca | act | cag | gaa | gac | 1088 |
|---|---|---|---|---|---|---|---|---|---|---|---|---|---|---|---|---|
| Gln | Ile | Gln | Lys | Ser | Pro | Glu | Pro | Glu | Val | Leu | Ser | Thr | Gln | Glu | Asp |  |
| 290 |  |  |  |  | 295 |  |  |  |  | 300 |  |  |  |  | 305 |  |

| ttg | ttt | gac | cag | agc | aat | aaa | aca | gta | tct | tct | gat | ggt | tgc | tct | act | 1136 |
|---|---|---|---|---|---|---|---|---|---|---|---|---|---|---|---|---|
| Leu | Phe | Asp | Gln | Ser | Asn | Lys | Thr | Val | Ser | Ser | Asp | Gly | Cys | Ser | Thr |  |
|  |  |  |  | 310 |  |  |  |  | 315 |  |  |  |  | 320 |  |  |

| cct | tca | agg | gag | gaa | ggt | ggg | tgt | tct | ttg | gct | tcc | act | cct | gcc | acc | 1184 |
|---|---|---|---|---|---|---|---|---|---|---|---|---|---|---|---|---|
| Pro | Ser | Arg | Glu | Glu | Gly | Gly | Cys | Ser | Leu | Ala | Ser | Thr | Pro | Ala | Thr |  |
|  |  |  | 325 |  |  |  |  | 330 |  |  |  |  | 335 |  |  |  |

| act | ctg | cat | ctc | ctg | cag | ctc | tct | ggt | cag | agg | tcc | ctt | gtt | cag | gac | 1232 |
|---|---|---|---|---|---|---|---|---|---|---|---|---|---|---|---|---|
| Thr | Leu | His | Leu | Leu | Gln | Leu | Ser | Gly | Gln | Arg | Ser | Leu | Val | Gln | Asp |  |
|  |  | 340 |  |  |  |  | 345 |  |  |  |  | 350 |  |  |  |  |

| agt | ctt | tcc | acg | aat | tct | tca | gat | ctt | gtt | gct | cct | tct | cct | gat | gct | 1280 |
|---|---|---|---|---|---|---|---|---|---|---|---|---|---|---|---|---|
| Ser | Leu | Ser | Thr | Asn | Ser | Ser | Asp | Leu | Val | Ala | Pro | Ser | Pro | Asp | Ala |  |
| 355 |  |  |  |  | 360 |  |  |  |  | 365 |  |  |  |  |  |  |

| ttc | cga | tct | act | cct | ttt | atc | gtt | cct | agc | agt | ccc | aca | gag | caa | gaa | 1328 |
|---|---|---|---|---|---|---|---|---|---|---|---|---|---|---|---|---|
| Phe | Arg | Ser | Thr | Pro | Phe | Ile | Val | Pro | Ser | Ser | Pro | Thr | Glu | Gln | Glu |  |
| 370 |  |  |  |  | 375 |  |  |  |  | 380 |  |  |  |  | 385 |  |

| ggg | aga | caa | gat | aag | cca | atg | gac | acg | tca | gtg | tta | tct | gaa | gaa | gga | 1376 |
|---|---|---|---|---|---|---|---|---|---|---|---|---|---|---|---|---|
| Gly | Arg | Gln | Asp | Lys | Pro | Met | Asp | Thr | Ser | Val | Leu | Ser | Glu | Glu | Gly |  |
|  |  |  | 390 |  |  |  |  | 395 |  |  |  |  | 400 |  |  |  |

| gga | gag | cct | ttt | cag | aag | aaa | ctt | caa | agt | ggt | gaa | cca | gtg | gag | tta | 1424 |
|---|---|---|---|---|---|---|---|---|---|---|---|---|---|---|---|---|
| Gly | Glu | Pro | Phe | Gln | Lys | Lys | Leu | Gln | Ser | Gly | Glu | Pro | Val | Glu | Leu |  |
|  |  | 405 |  |  |  |  | 410 |  |  |  |  | 415 |  |  |  |  |

| gaa | aac | ccc | cct | ctc | ctg | cct | gag | tcc | act | gta | tca | cca | caa | gcc | tca | 1472 |
|---|---|---|---|---|---|---|---|---|---|---|---|---|---|---|---|---|
| Glu | Asn | Pro | Pro | Leu | Leu | Pro | Glu | Ser | Thr | Val | Ser | Pro | Gln | Ala | Ser |  |
|  |  | 420 |  |  |  |  | 425 |  |  |  |  | 430 |  |  |  |  |

| aca | cca | ata | tct | cag | agc | aca | cca | gtc | ttc | cct | cct | ggg | tca | ctt | cct | 1520 |
|---|---|---|---|---|---|---|---|---|---|---|---|---|---|---|---|---|
| Thr | Pro | Ile | Ser | Gln | Ser | Thr | Pro | Val | Phe | Pro | Pro | Gly | Ser | Leu | Pro |  |
| 435 |  |  |  |  | 440 |  |  |  |  | 445 |  |  |  |  |  |  |

| atc | cca | tcc | cag | cct | cag | ttt | tct | cat | gac | att | ttt | att | cct | tcc | cca | 1568 |
|---|---|---|---|---|---|---|---|---|---|---|---|---|---|---|---|---|
| Ile | Pro | Ser | Gln | Pro | Gln | Phe | Ser | His | Asp | Ile | Phe | Ile | Pro | Ser | Pro |  |
| 450 |  |  |  |  | 455 |  |  |  |  | 460 |  |  |  |  | 465 |  |

| agt | ctg | gaa | gaa | caa | tca | aat | gat | ggg | aag | aaa | gat | gga | gat | atg | cat | 1616 |
|---|---|---|---|---|---|---|---|---|---|---|---|---|---|---|---|---|
| Ser | Leu | Glu | Glu | Gln | Ser | Asn | Asp | Gly | Lys | Lys | Asp | Gly | Asp | Met | His |  |
|  |  |  |  | 470 |  |  |  |  | 475 |  |  |  |  | 480 |  |  |

| agt | tca | tct | ttg | aca | gtt | gag | tgt | tct | aaa | act | tca | gag | att | gaa | cca | 1664 |
|---|---|---|---|---|---|---|---|---|---|---|---|---|---|---|---|---|
| Ser | Ser | Ser | Leu | Thr | Val | Glu | Cys | Ser | Lys | Thr | Ser | Glu | Ile | Glu | Pro |  |
|  |  |  | 485 |  |  |  |  | 490 |  |  |  |  | 495 |  |  |  |

| aag | aat | tcc | cct | gag | gat | ctt | ggg | cta | tct | ttg | aca | ggg | gat | tct | tgc | 1712 |
|---|---|---|---|---|---|---|---|---|---|---|---|---|---|---|---|---|
| Lys | Asn | Ser | Pro | Glu | Asp | Leu | Gly | Leu | Ser | Leu | Thr | Gly | Asp | Ser | Cys |  |
|  |  | 500 |  |  |  |  | 505 |  |  |  |  | 510 |  |  |  |  |

```
aag ttg atg ctt tct aca agt gaa tat agt cag tcc cca aag atg gag       1760
Lys Leu Met Leu Ser Thr Ser Glu Tyr Ser Gln Ser Pro Lys Met Glu
515                 520                 525 agc ttg agt tct cac aga att gat gaa gat gga gaa aac aca cag att       1808
Ser Leu Ser Ser His Arg Ile Asp Glu Asp Gly Glu Asn Thr Gln Ile
530                 535                 540                 545 gag gat acg gaa ccc atg tct cca gtt ctc aat tct aaa ttt gtt cct       1856
Glu Asp Thr Glu Pro Met Ser Pro Val Leu Asn Ser Lys Phe Val Pro
                550                 555                 560 gct gaa aat gat agt atc ctg atg aat cca gca cag gat ggt gaa gta       1904
Ala Glu Asn Asp Ser Ile Leu Met Asn Pro Ala Gln Asp Gly Glu Val
            565                 570                 575 caa ctg agt cag aat gat gac aaa aca aag gga gat gat aca gac acc       1952
Gln Leu Ser Gln Asn Asp Asp Lys Thr Lys Gly Asp Asp Thr Asp Thr
        580                 585                 590 agg gat gac att agt att tta gcc act ggt tgc aag ggc aga gaa gaa       2000
Arg Asp Asp Ile Ser Ile Leu Ala Thr Gly Cys Lys Gly Arg Glu Glu
595                 600                 605 acg gta gca gaa gat gtt tgt att gat ctc act tgt gat tcg ggg agt       2048
Thr Val Ala Glu Asp Val Cys Ile Asp Leu Thr Cys Asp Ser Gly Ser
610                 615                 620                 625 cag gca gtt ccg tca cca gct act cga tct gag gca ctt tct agt gtg       2096
Gln Ala Val Pro Ser Pro Ala Thr Arg Ser Glu Ala Leu Ser Ser Val
                630                 635                 640 tta gat cag gag gaa gct atg gaa att aaa gaa cac cat cca gag gag       2144
Leu Asp Gln Glu Glu Ala Met Glu Ile Lys Glu His His Pro Glu Glu
            645                 650                 655 ggg tct tca ggg tct gag gtg gaa gaa atc cct gag aca cct tgt gaa       2192
Gly Ser Ser Gly Ser Glu Val Glu Glu Ile Pro Glu Thr Pro Cys Glu
        660                 665                 670 agt caa gga gag gaa ctc aaa gaa gaa aat atg gag agt gtt ccg ttg       2240
Ser Gln Gly Glu Glu Leu Lys Glu Glu Asn Met Glu Ser Val Pro Leu
675                 680                 685 cac ctt tct ctg act gaa act cag tcc caa ggg ttg tgt ctt caa aag       2288
His Leu Ser Leu Thr Glu Thr Gln Ser Gln Gly Leu Cys Leu Gln Lys
690                 695                 700                 705 gaa atg cca aaa aaa gaa tgc tca gaa gct atg gaa gtt gaa acc agt       2336
Glu Met Pro Lys Lys Glu Cys Ser Glu Ala Met Glu Val Glu Thr Ser
                710                 715                 720 gtg att agt att gat tcc cct caa aag ttg gca ata ctt gac caa gaa       2384
Val Ile Ser Ile Asp Ser Pro Gln Lys Leu Ala Ile Leu Asp Gln Glu
            725                 730                 735 ttg gaa cat aag gaa cag gaa gct tgg gaa gaa gct act tca gag gac       2432
Leu Glu His Lys Glu Gln Glu Ala Trp Glu Glu Ala Thr Ser Glu Asp
        740                 745                 750 tcc agt gtt gtc att gta gat gtg aaa gag cca tct ccc aga gtt gat       2480
Ser Ser Val Val Ile Val Asp Val Lys Glu Pro Ser Pro Arg Val Asp
755                 760                 765 gtt tct tgt gaa cct ttg gag gga gtg gag aag tgc tca gat tcc cag       2528
Val Ser Cys Glu Pro Leu Glu Gly Val Glu Lys Cys Ser Asp Ser Gln
770                 775                 780                 785 tca tgg gag gat att gct cca gaa ata gaa cca tgt gct gag aat aga       2576
Ser Trp Glu Asp Ile Ala Pro Glu Ile Glu Pro Cys Ala Glu Asn Arg
                790                 795                 800 tta gac acc aag gaa gaa aag agt gta gaa tat gaa gga gat ctg aaa       2624
Leu Asp Thr Lys Glu Glu Lys Ser Val Glu Tyr Glu Gly Asp Leu Lys
            805                 810                 815 tca ggg act gca gaa aca gaa cct gta gag caa gat tct tca cag cct       2672
Ser Gly Thr Ala Glu Thr Glu Pro Val Glu Gln Asp Ser Ser Gln Pro
        820                 825                 830
```

-continued

| | |
|---|---|
| tcc tta cct tta gtg aga gca gat gat cct tta aga ctt gac cag gag<br>Ser Leu Pro Leu Val Arg Ala Asp Asp Pro Leu Arg Leu Asp Gln Glu<br>835                               840                          845 | 2720 |
| ttg cag cag ccc caa act cag gag aaa aca agt aat tca tta aca gaa<br>Leu Gln Gln Pro Gln Thr Gln Glu Lys Thr Ser Asn Ser Leu Thr Glu<br>850                               855                       860                   865 | 2768 |
| gac tca aaa atg gct aat gca aag cag cta agc tca gat gca gag gcc<br>Asp Ser Lys Met Ala Asn Ala Lys Gln Leu Ser Ser Asp Ala Glu Ala<br>                      870                       875                       880 | 2816 |
| cag aag ctg ggg aag ccc tct gcc cat gcc tca caa agc ttc tgt gaa<br>Gln Lys Leu Gly Lys Pro Ser Ala His Ala Ser Gln Ser Phe Cys Glu<br>             885                       890                       895 | 2864 |
| agt tct agt gaa acc cca ttt cat ttc act ttg cct aaa gaa ggt gat<br>Ser Ser Ser Glu Thr Pro Phe His Phe Thr Leu Pro Lys Glu Gly Asp<br>                900                       905                       910 | 2912 |
| atc atc cca cca ttg act ggt gca acc cca cct ctt att ggg cac cta<br>Ile Ile Pro Pro Leu Thr Gly Ala Thr Pro Pro Leu Ile Gly His Leu<br>             915                       920                       925 | 2960 |
| aaa ttg gag ccc aag aga cac agt act cct att ggt att agc aac tat<br>Lys Leu Glu Pro Lys Arg His Ser Thr Pro Ile Gly Ile Ser Asn Tyr<br>930                               935                       940                   945 | 3008 |
| cca gaa agc acc ata gca acc agt gat gtc atg tct gaa agc atg gtg<br>Pro Glu Ser Thr Ile Ala Thr Ser Asp Val Met Ser Glu Ser Met Val<br>                      950                       955                       960 | 3056 |
| gag acc cat gat ccc ata ctt ggg agt gga aaa ggg gat tct ggg gct<br>Glu Thr His Asp Pro Ile Leu Gly Ser Gly Lys Gly Asp Ser Gly Ala<br>             965                       970                       975 | 3104 |
| gcc cca gac gtg gat gat aaa tta tgt cta aga atg aaa ctg gtt agt<br>Ala Pro Asp Val Asp Asp Lys Leu Cys Leu Arg Met Lys Leu Val Ser<br>                980                       985                       990 | 3152 |
| cct gag act gag gcg agt gaa   gag tct ttg cag ttc   aac ctg gaa aag<br>Pro Glu Thr Glu Ala Ser Glu   Glu Ser Leu Gln Phe   Asn Leu Glu Lys<br>995                               1000                      1005 | 3200 |
| cct   gca act ggt gaa aga   aaa aat gga tct act   gct gtt gct gag<br>Pro   Ala Thr Gly Glu Arg   Lys Asn Gly Ser Thr   Ala Val Ala Glu<br>1010                         1015                      1020 | 3245 |
| tct gtt gcc agt ccc cag aag acc atg tct gtg ttg agc tgt atc<br>Ser Val Ala Ser Pro Gln Lys Thr Met Ser Val Leu Ser Cys Ile<br>1025                       1030                     1035 | 3290 |
| tgt gaa gcc agg caa gag aat gag gct cga agt gag gat ccc ccc<br>Cys Glu Ala Arg Gln Glu Asn Glu Ala Arg Ser Glu Asp Pro Pro<br>1040                       1045                     1050 | 3335 |
| acc aca ccc atc agg ggg aac ttg ctc cac ttt cca agt tct caa<br>Thr Thr Pro Ile Arg Gly Asn Leu Leu His Phe Pro Ser Ser Gln<br>1055                       1060                     1065 | 3380 |
| gga gaa gag gag aaa gaa aaa ttg gag ggt gac cat aca atc agg<br>Gly Glu Glu Glu Lys Glu Lys Leu Glu Gly Asp His Thr Ile Arg<br>1070                       1075                     1080 | 3425 |
| cag agt caa cag cct atg aag ccc att agt cct gtc aag gac cct<br>Gln Ser Gln Gln Pro Met Lys Pro Ile Ser Pro Val Lys Asp Pro<br>1085                       1090                     1095 | 3470 |
| gtt tct cct gct tcc cag aag atg gtc ata caa ggg cca tcc agt<br>Val Ser Pro Ala Ser Gln Lys Met Val Ile Gln Gly Pro Ser Ser<br>1100                       1105                     1110 | 3515 |
| cct caa gga gag gca atg gtg aca gat gtg cta gaa gac cag aaa<br>Pro Gln Gly Glu Ala Met Val Thr Asp Val Leu Glu Asp Gln Lys<br>1115                       1120                     1125 | 3560 |
| gaa gga cgg agt act aat aag gaa aat cct agt aag gcc ttg att<br>Glu Gly Arg Ser Thr Asn Lys Glu Asn Pro Ser Lys Ala Leu Ile | 3605 |

-continued

| | | | | | | | | | | | | | | | |
|---|---|---|---|---|---|---|---|---|---|---|---|---|---|---|---|
| | | 1130 | | | | 1135 | | | | | 1140 | | | | |
| gaa | agg | ccc | agc | caa | aat | aac | ata | gga | atc | caa | acc | atg | gag | tgt | 3650 |
| Glu | Arg | Pro | Ser | Gln | Asn | Asn | Ile | Gly | Ile | Gln | Thr | Met | Glu | Cys | |
| 1145 | | | | | 1150 | | | | | 1155 | | | | | |
| tcc | ttg | agg | gtc | cca | gaa | act | gtt | tca | gca | gca | acc | cag | act | ata | 3695 |
| Ser | Leu | Arg | Val | Pro | Glu | Thr | Val | Ser | Ala | Ala | Thr | Gln | Thr | Ile | |
| 1160 | | | | | 1165 | | | | | 1170 | | | | | |
| aag | aat | gtg | tgt | gag | cag | ggg | acc | agt | aca | gtg | gac | cag | aac | ttt | 3740 |
| Lys | Asn | Val | Cys | Glu | Gln | Gly | Thr | Ser | Thr | Val | Asp | Gln | Asn | Phe | |
| 1175 | | | | | 1180 | | | | | 1185 | | | | | |
| gga | aag | caa | gat | gcc | aca | gtt | cag | act | gag | agg | ggg | agt | ggt | gag | 3785 |
| Gly | Lys | Gln | Asp | Ala | Thr | Val | Gln | Thr | Glu | Arg | Gly | Ser | Gly | Glu | |
| 1190 | | | | | 1195 | | | | | 1200 | | | | | |
| aaa | cca | gtc | agt | gct | cct | ggg | gat | gat | aca | gag | tcg | ctc | cat | agc | 3830 |
| Lys | Pro | Val | Ser | Ala | Pro | Gly | Asp | Asp | Thr | Glu | Ser | Leu | His | Ser | |
| 1205 | | | | | 1210 | | | | | 1215 | | | | | |
| cag | gga | gaa | gaa | gag | ttt | gat | atg | cct | cag | cct | cca | cat | ggc | cat | 3875 |
| Gln | Gly | Glu | Glu | Glu | Phe | Asp | Met | Pro | Gln | Pro | Pro | His | Gly | His | |
| 1220 | | | | | 1225 | | | | | 1230 | | | | | |
| gtc | tta | cat | cgt | cac | atg | aga | aca | atc | cgg | gaa | gta | cgc | aca | ctt | 3920 |
| Val | Leu | His | Arg | His | Met | Arg | Thr | Ile | Arg | Glu | Val | Arg | Thr | Leu | |
| 1235 | | | | | 1240 | | | | | 1245 | | | | | |
| gtc | act | cgt | gtc | att | aca | gat | gtg | tat | tat | gtg | gat | gga | aca | gaa | 3965 |
| Val | Thr | Arg | Val | Ile | Thr | Asp | Val | Tyr | Tyr | Val | Asp | Gly | Thr | Glu | |
| 1250 | | | | | 1255 | | | | | 1260 | | | | | |
| gta | gaa | aga | aaa | gta | act | gag | gag | act | gaa | gag | cca | att | gta | gag | 4010 |
| Val | Glu | Arg | Lys | Val | Thr | Glu | Glu | Thr | Glu | Glu | Pro | Ile | Val | Glu | |
| 1265 | | | | | 1270 | | | | | 1275 | | | | | |
| tgt | cag | gag | tgt | gaa | act | gaa | gtt | tcc | cct | tca | cag | act | ggg | ggc | 4055 |
| Cys | Gln | Glu | Cys | Glu | Thr | Glu | Val | Ser | Pro | Ser | Gln | Thr | Gly | Gly | |
| 1280 | | | | | 1285 | | | | | 1290 | | | | | |
| tcc | tca | ggt | gac | ctg | ggg | gat | atc | agc | tcc | ttc | tcc | tcc | aag | gca | 4100 |
| Ser | Ser | Gly | Asp | Leu | Gly | Asp | Ile | Ser | Ser | Phe | Ser | Ser | Lys | Ala | |
| 1295 | | | | | 1300 | | | | | 1305 | | | | | |
| tcc | agc | tta | cac | cgc | aca | tca | agt | ggg | aca | agt | ctc | tca | gct | atg | 4145 |
| Ser | Ser | Leu | His | Arg | Thr | Ser | Ser | Gly | Thr | Ser | Leu | Ser | Ala | Met | |
| 1310 | | | | | 1315 | | | | | 1320 | | | | | |
| cac | agc | agt | gga | agc | tca | ggg | aaa | gga | gcc | gga | cca | ctc | aga | ggg | 4190 |
| His | Ser | Ser | Gly | Ser | Ser | Gly | Lys | Gly | Ala | Gly | Pro | Leu | Arg | Gly | |
| 1325 | | | | | 1330 | | | | | 1335 | | | | | |
| aaa | acc | agc | ggg | aca | gaa | ccc | gca | gat | ttt | gcc | tta | ccc | agc | tcc | 4235 |
| Lys | Thr | Ser | Gly | Thr | Glu | Pro | Ala | Asp | Phe | Ala | Leu | Pro | Ser | Ser | |
| 1340 | | | | | 1345 | | | | | 1350 | | | | | |
| cga | gga | ggc | cca | gga | aaa | ctg | agt | cct | aga | aaa | ggg | gtc | agt | cag | 4280 |
| Arg | Gly | Gly | Pro | Gly | Lys | Leu | Ser | Pro | Arg | Lys | Gly | Val | Ser | Gln | |
| 1355 | | | | | 1360 | | | | | 1365 | | | | | |
| aca | ggg | acg | cca | gtg | tgt | gag | gag | gat | ggt | gat | gca | ggc | ctt | ggc | 4325 |
| Thr | Gly | Thr | Pro | Val | Cys | Glu | Glu | Asp | Gly | Asp | Ala | Gly | Leu | Gly | |
| 1370 | | | | | 1375 | | | | | 1380 | | | | | |
| atc | aga | cag | gga | ggg | aag | gct | cca | gtc | acg | cct | cgt | ggg | cgt | ggg | 4370 |
| Ile | Arg | Gln | Gly | Gly | Lys | Ala | Pro | Val | Thr | Pro | Arg | Gly | Arg | Gly | |
| 1385 | | | | | 1390 | | | | | 1395 | | | | | |
| cga | agg | ggc | cgc | cca | cct | tct | cgg | acc | act | gga | acc | aga | gaa | aca | 4415 |
| Arg | Arg | Gly | Arg | Pro | Pro | Ser | Arg | Thr | Thr | Gly | Thr | Arg | Glu | Thr | |
| 1400 | | | | | 1405 | | | | | 1410 | | | | | |
| gct | gtg | cct | ggc | ccc | ttg | ggc | ata | gag | gac | att | tca | cct | aac | ttg | 4460 |
| Ala | Val | Pro | Gly | Pro | Leu | Gly | Ile | Glu | Asp | Ile | Ser | Pro | Asn | Leu | |
| 1415 | | | | | 1420 | | | | | 1425 | | | | | |
| tca | cca | gat | gat | aaa | tcc | ttc | agc | cgt | gtc | gtg | ccc | cga | gtg | cca | 4505 |

```
Ser Pro Asp Asp Lys Ser Phe Ser Arg Val Val Pro Arg Val Pro
1430                1435                1440 gac tcc acc aga cga aca gat gtg ggt gct ggt gct ttg cgt cgt    4550
Asp Ser Thr Arg Arg Thr Asp Val Gly Ala Gly Ala Leu Arg Arg
1445                1450                1455 agt gac tct cca gaa att cct ttc cag gct gct gct ggc cct tct    4595
Ser Asp Ser Pro Glu Ile Pro Phe Gln Ala Ala Ala Gly Pro Ser
1460                1465                1470 gat ggc tta gat gcc tcc tct cca gga aat agc ttt gta ggg ctc    4640
Asp Gly Leu Asp Ala Ser Ser Pro Gly Asn Ser Phe Val Gly Leu
1475                1480                1485 cgt gtt gta gcc aag tgg tca tcc aat ggc tac ttt tac tct ggg    4685
Arg Val Val Ala Lys Trp Ser Ser Asn Gly Tyr Phe Tyr Ser Gly
1490                1495                1500 aaa atc aca cga gat gtc gga gct ggg aag tat aaa ttg ctc ttt    4730
Lys Ile Thr Arg Asp Val Gly Ala Gly Lys Tyr Lys Leu Leu Phe
1505                1510                1515 gat gat ggg tac gaa tgt gat gtg ttg ggc aaa gac att ctg tta    4775
Asp Asp Gly Tyr Glu Cys Asp Val Leu Gly Lys Asp Ile Leu Leu
1520                1525                1530 tgt gac ccc atc ccg ctg gac act gaa gtg acg gcc ctc tcg gag    4820
Cys Asp Pro Ile Pro Leu Asp Thr Glu Val Thr Ala Leu Ser Glu
1535                1540                1545 gat gag tat ttc agt gca gga gtg gtg aaa gga cat agg aag gag    4865
Asp Glu Tyr Phe Ser Ala Gly Val Val Lys Gly His Arg Lys Glu
1550                1555                1560 tct ggg gaa ctg tac tac agc att gaa aaa gaa ggc caa aga aag    4910
Ser Gly Glu Leu Tyr Tyr Ser Ile Glu Lys Glu Gly Gln Arg Lys
1565                1570                1575 tgg tat aag cga atg gct gtc atc ctg tcc ttg gag caa gga aac    4955
Trp Tyr Lys Arg Met Ala Val Ile Leu Ser Leu Glu Gln Gly Asn
1580                1585                1590 aga ctg aga gag cag tat ggg ctt ggc ccc tat gaa gca gta aca    5000
Arg Leu Arg Glu Gln Tyr Gly Leu Gly Pro Tyr Glu Ala Val Thr
1595                1600                1605 cct ctt aca aag gca gca gat atc agc tta gac aat ttg gtg gaa    5045
Pro Leu Thr Lys Ala Ala Asp Ile Ser Leu Asp Asn Leu Val Glu
1610                1615                1620 ggg aag cgg aaa cgg cgc agt aac gtc agc tcc cca gcc acc cct    5090
Gly Lys Arg Lys Arg Arg Ser Asn Val Ser Ser Pro Ala Thr Pro
1625                1630                1635 act gcc tcc agt agc agc agc aca acc cct acc cga aag atc aca    5135
Thr Ala Ser Ser Ser Ser Ser Thr Thr Pro Thr Arg Lys Ile Thr
1640                1645                1650 gaa agt cct cgt gcc tcc atg gga gtt ctc tca ggc aaa aga aaa    5180
Glu Ser Pro Arg Ala Ser Met Gly Val Leu Ser Gly Lys Arg Lys
1655                1660                1665 ctt atc act tct gaa gag gaa cgg tcc cct gcc aag cga ggt cgc    5225
Leu Ile Thr Ser Glu Glu Glu Arg Ser Pro Ala Lys Arg Gly Arg
1670                1675                1680 aag tct gcc aca gta aaa cct ggt gca gta ggg gca gga gag ttt    5270
Lys Ser Ala Thr Val Lys Pro Gly Ala Val Gly Ala Gly Glu Phe
1685                1690                1695 gtg agc ccc tgt gag agt gga gac aac acc ggt gaa ccc tct gcc    5315
Val Ser Pro Cys Glu Ser Gly Asp Asn Thr Gly Glu Pro Ser Ala
1700                1705                1710 ctg gaa gag cag aga ggg cct ttg cct ctc aac aag acc ttg ttt    5360
Leu Glu Glu Gln Arg Gly Pro Leu Pro Leu Asn Lys Thr Leu Phe
1715                1720                1725
```

|     |     |     |     |     |     |     |     |     |     |     |     |     |     |     | |
|---|---|---|---|---|---|---|---|---|---|---|---|---|---|---|---|
| ctg | ggc | tac | gca | ttt | ctc | ctt | acc | atg | gcc | aca | acc | agt | gac | aag | 5405 |
| Leu | Gly | Tyr | Ala | Phe | Leu | Leu | Thr | Met | Ala | Thr | Thr | Ser | Asp | Lys | |
| 1730 | | | | 1735 | | | | | 1740 | | | | | | |
| ttg | gcc | agc | cgc | tcc | aaa | ctg | cca | gat | ggt | cct | aca | gga | agc | agt | 5450 |
| Leu | Ala | Ser | Arg | Ser | Lys | Leu | Pro | Asp | Gly | Pro | Thr | Gly | Ser | Ser | |
| 1745 | | | | 1750 | | | | | 1755 | | | | | | |
| gaa | gag | gag | gag | gaa | ttt | ttg | gaa | att | cct | cct | ttc | aac | aag | cag | 5495 |
| Glu | Glu | Glu | Glu | Glu | Phe | Leu | Glu | Ile | Pro | Pro | Phe | Asn | Lys | Gln | |
| 1760 | | | | 1765 | | | | | 1770 | | | | | | |
| tat | aca | gaa | tcc | cag | ctt | cga | gca | gga | gct | ggc | tat | atc | ctt | gaa | 5540 |
| Tyr | Thr | Glu | Ser | Gln | Leu | Arg | Ala | Gly | Ala | Gly | Tyr | Ile | Leu | Glu | |
| 1775 | | | | 1780 | | | | | 1785 | | | | | | |
| gat | ttc | aat | gaa | gcc | cag | tgt | aac | aca | gct | tac | cag | tgt | ctt | cta | 5585 |
| Asp | Phe | Asn | Glu | Ala | Gln | Cys | Asn | Thr | Ala | Tyr | Gln | Cys | Leu | Leu | |
| 1790 | | | | 1795 | | | | | 1800 | | | | | | |
| att | gcg | gat | cag | cat | tgt | cga | acc | cgg | aag | tac | ttc | ctg | tgc | ctt | 5630 |
| Ile | Ala | Asp | Gln | His | Cys | Arg | Thr | Arg | Lys | Tyr | Phe | Leu | Cys | Leu | |
| 1805 | | | | 1810 | | | | | 1815 | | | | | | |
| gcc | agt | ggg | att | cct | tgt | gtg | tct | cat | gtc | tgg | gtc | cat | gat | agt | 5675 |
| Ala | Ser | Gly | Ile | Pro | Cys | Val | Ser | His | Val | Trp | Val | His | Asp | Ser | |
| 1820 | | | | 1825 | | | | | 1830 | | | | | | |
| tgc | cat | gcc | aac | cag | ctc | cag | aac | tac | cgt | aat | tat | ctg | ttg | cca | 5720 |
| Cys | His | Ala | Asn | Gln | Leu | Gln | Asn | Tyr | Arg | Asn | Tyr | Leu | Leu | Pro | |
| 1835 | | | | 1840 | | | | | 1845 | | | | | | |
| gct | ggg | tac | agc | ctt | gag | gag | caa | aga | att | ctg | gac | tgg | caa | ccc | 5765 |
| Ala | Gly | Tyr | Ser | Leu | Glu | Glu | Gln | Arg | Ile | Leu | Asp | Trp | Gln | Pro | |
| 1850 | | | | 1855 | | | | | 1860 | | | | | | |
| cgt | gaa | aat | cct | ttc | cag | aat | ctg | aag | gta | ctc | ttg | gta | tca | gac | 5810 |
| Arg | Glu | Asn | Pro | Phe | Gln | Asn | Leu | Lys | Val | Leu | Leu | Val | Ser | Asp | |
| 1865 | | | | 1870 | | | | | 1875 | | | | | | |
| caa | cag | cag | aac | ttc | ctg | gag | ctc | tgg | tct | gag | atc | ctc | atg | act | 5855 |
| Gln | Gln | Gln | Asn | Phe | Leu | Glu | Leu | Trp | Ser | Glu | Ile | Leu | Met | Thr | |
| 1880 | | | | 1885 | | | | | 1890 | | | | | | |
| ggt | ggt | gca | gcc | tct | gtg | aag | cag | cac | cat | tca | agt | gcc | cat | aac | 5900 |
| Gly | Gly | Ala | Ala | Ser | Val | Lys | Gln | His | His | Ser | Ser | Ala | His | Asn | |
| 1895 | | | | 1900 | | | | | 1905 | | | | | | |
| aaa | gat | att | gct | tta | ggg | gta | ttt | gat | gtg | gtg | gtg | acg | gac | ccc | 5945 |
| Lys | Asp | Ile | Ala | Leu | Gly | Val | Phe | Asp | Val | Val | Val | Thr | Asp | Pro | |
| 1910 | | | | 1915 | | | | | 1920 | | | | | | |
| tca | tgc | cca | gcc | tcg | gtg | ctg | aag | tgt | gct | gaa | gca | ttg | cag | ctg | 5990 |
| Ser | Cys | Pro | Ala | Ser | Val | Leu | Lys | Cys | Ala | Glu | Ala | Leu | Gln | Leu | |
| 1925 | | | | 1930 | | | | | 1935 | | | | | | |
| cct | gtg | gtg | tca | caa | gag | tgg | gtg | atc | cag | tgc | ctc | att | gtt | ggg | 6035 |
| Pro | Val | Val | Ser | Gln | Glu | Trp | Val | Ile | Gln | Cys | Leu | Ile | Val | Gly | |
| 1940 | | | | 1945 | | | | | 1950 | | | | | | |
| gag | aga | att | gga | ttc | aag | cag | cat | cca | aaa | tat | aaa | cac | gat | tat | 6080 |
| Glu | Arg | Ile | Gly | Phe | Lys | Gln | His | Pro | Lys | Tyr | Lys | His | Asp | Tyr | |
| 1955 | | | | 1960 | | | | | 1965 | | | | | | |
| gtt | tct | cac | taaagatact tggtcttact ggttttattc cctgctatcg | | | | | | | | | | | | 6129 |
| Val | Ser | His | | | | | | | | | | | | | |
| 1970 | | | | | | | | | | | | | | | | tggagattgt gttttaacca ggttttaaat gtgtcttgtg tgtaactgga ttccttgcat    6189 ggatcttgta tatagtttta tttgctgaac ttttatgata aaataaatgt tgaatctctt    6249 tggttgtagt aactggg    6266

<210> SEQ ID NO 2
<211> LENGTH: 1972
<212> TYPE: PRT
<213> ORGANISM: human 53Bp1

<400> SEQUENCE: 2

```
Met Asp Pro Thr Gly Ser Gln Leu Asp Ser Asp Phe Ser Gln Gln Asp
1               5                   10                  15

Thr Pro Cys Leu Ile Ile Glu Asp Ser Gln Pro Glu Ser Gln Val Leu
            20                  25                  30

Glu Asp Asp Ser Gly Ser His Phe Ser Met Leu Ser Arg His Leu Pro
        35                  40                  45

Asn Leu Gln Thr His Lys Glu Asn Pro Val Leu Asp Val Val Ser Asn
    50                  55                  60

Pro Glu Gln Thr Ala Gly Glu Glu Arg Gly Asp Gly Asn Ser Gly Phe
65                  70                  75                  80

Asn Glu His Leu Lys Glu Asn Lys Val Ala Asp Pro Val Asp Ser Ser
                85                  90                  95

Asn Leu Asp Thr Cys Gly Ser Ile Ser Gln Val Ile Glu Gln Leu Pro
            100                 105                 110

Gln Pro Asn Arg Thr Ser Ser Val Leu Gly Met Ser Val Glu Ser Ala
            115                 120                 125

Pro Ala Val Glu Glu Lys Gly Glu Glu Leu Glu Gln Lys Glu Lys
        130                 135                 140

Glu Lys Glu Glu Asp Thr Ser Gly Asn Thr Thr His Ser Leu Gly Ala
145                 150                 155                 160

Glu Asp Thr Ala Ser Ser Gln Leu Gly Phe Gly Val Leu Glu Leu Ser
            165                 170                 175

Gln Ser Gln Asp Val Glu Glu Asn Thr Val Pro Tyr Glu Val Asp Lys
            180                 185                 190

Glu Gln Leu Gln Ser Val Thr Thr Asn Ser Gly Tyr Thr Arg Leu Ser
            195                 200                 205

Asp Val Asp Ala Asn Thr Ala Ile Lys His Glu Glu Gln Ser Asn Glu
            210                 215                 220

Asp Ile Pro Ile Ala Glu Gln Ser Ser Lys Asp Ile Pro Val Thr Ala
225                 230                 235                 240

Gln Pro Ser Lys Asp Val His Val Val Lys Glu Gln Asn Pro Pro Pro
            245                 250                 255

Ala Arg Ser Glu Asp Met Pro Phe Ser Pro Lys Ala Ser Val Ala Ala
            260                 265                 270

Met Glu Ala Lys Glu Gln Leu Ser Ala Gln Glu Leu Met Glu Ser Gly
            275                 280                 285

Leu Gln Ile Gln Lys Ser Pro Glu Pro Glu Val Leu Ser Thr Gln Glu
            290                 295                 300

Asp Leu Phe Asp Gln Ser Asn Lys Thr Val Ser Ser Asp Gly Cys Ser
305                 310                 315                 320

Thr Pro Ser Arg Glu Glu Gly Gly Cys Ser Leu Ala Ser Thr Pro Ala
            325                 330                 335

Thr Thr Leu His Leu Leu Gln Leu Ser Gly Gln Arg Ser Leu Val Gln
            340                 345                 350

Asp Ser Leu Ser Thr Asn Ser Ser Asp Leu Val Ala Pro Ser Pro Asp
            355                 360                 365

Ala Phe Arg Ser Thr Pro Phe Ile Val Pro Ser Ser Pro Thr Glu Gln
            370                 375                 380

Glu Gly Arg Gln Asp Lys Pro Met Asp Thr Ser Val Leu Ser Glu Glu
385                 390                 395                 400

Gly Gly Glu Pro Phe Gln Lys Lys Leu Gln Ser Gly Glu Pro Val Glu
```

-continued

```
                405                 410                 415
Leu Glu Asn Pro Pro Leu Leu Pro Glu Ser Thr Val Ser Pro Gln Ala
                420                 425                 430
Ser Thr Pro Ile Ser Gln Ser Thr Pro Val Phe Pro Pro Gly Ser Leu
            435                 440                 445
Pro Ile Pro Ser Gln Pro Gln Phe Ser His Asp Ile Phe Ile Pro Ser
        450                 455                 460
Pro Ser Leu Glu Glu Gln Ser Asn Asp Gly Lys Lys Asp Gly Asp Met
465                 470                 475                 480
His Ser Ser Ser Leu Thr Val Glu Cys Ser Lys Thr Ser Glu Ile Glu
                485                 490                 495
Pro Lys Asn Ser Pro Glu Asp Leu Gly Leu Ser Leu Thr Gly Asp Ser
            500                 505                 510
Cys Lys Leu Met Leu Ser Thr Ser Glu Tyr Ser Gln Ser Pro Lys Met
        515                 520                 525
Glu Ser Leu Ser Ser His Arg Ile Asp Glu Asp Gly Glu Asn Thr Gln
        530                 535                 540
Ile Glu Asp Thr Glu Pro Met Ser Pro Val Leu Asn Ser Lys Phe Val
545                 550                 555                 560
Pro Ala Glu Asn Asp Ser Ile Leu Met Asn Pro Ala Gln Asp Gly Glu
                565                 570                 575
Val Gln Leu Ser Gln Asn Asp Asp Lys Thr Lys Gly Asp Asp Thr Asp
            580                 585                 590
Thr Arg Asp Asp Ile Ser Ile Leu Ala Thr Gly Cys Lys Gly Arg Glu
        595                 600                 605
Glu Thr Val Ala Glu Asp Val Cys Ile Asp Leu Thr Cys Asp Ser Gly
        610                 615                 620
Ser Gln Ala Val Pro Ser Pro Ala Thr Arg Ser Glu Ala Leu Ser Ser
625                 630                 635                 640
Val Leu Asp Gln Glu Glu Ala Met Glu Ile Lys Glu His His Pro Glu
                645                 650                 655
Glu Gly Ser Ser Gly Ser Glu Val Glu Glu Ile Pro Glu Thr Pro Cys
            660                 665                 670
Glu Ser Gln Gly Glu Glu Leu Lys Glu Glu Asn Met Glu Ser Val Pro
        675                 680                 685
Leu His Leu Ser Leu Thr Glu Thr Gln Ser Gln Gly Leu Cys Leu Gln
        690                 695                 700
Lys Glu Met Pro Lys Lys Glu Cys Ser Glu Ala Met Glu Val Glu Thr
705                 710                 715                 720
Ser Val Ile Ser Ile Asp Ser Pro Gln Lys Leu Ala Ile Leu Asp Gln
                725                 730                 735
Glu Leu Glu His Lys Glu Gln Glu Ala Trp Glu Glu Ala Thr Ser Glu
            740                 745                 750
Asp Ser Ser Val Val Ile Val Asp Val Lys Glu Pro Ser Pro Arg Val
        755                 760                 765
Asp Val Ser Cys Glu Pro Leu Glu Gly Val Glu Lys Cys Ser Asp Ser
        770                 775                 780
Gln Ser Trp Glu Asp Ile Ala Pro Glu Ile Glu Pro Cys Ala Glu Asn
785                 790                 795                 800
Arg Leu Asp Thr Lys Glu Lys Ser Val Glu Tyr Glu Gly Asp Leu
                805                 810                 815
Lys Ser Gly Thr Ala Glu Thr Glu Pro Val Glu Gln Asp Ser Ser Gln
            820                 825                 830
```

-continued

Pro Ser Leu Pro Leu Val Arg Ala Asp Asp Pro Leu Arg Leu Asp Gln
        835                 840                 845

Glu Leu Gln Gln Pro Gln Thr Gln Glu Lys Thr Ser Asn Ser Leu Thr
850                 855                 860

Glu Asp Ser Lys Met Ala Asn Ala Lys Gln Leu Ser Ser Asp Ala Glu
865                 870                 875                 880

Ala Gln Lys Leu Gly Lys Pro Ser Ala His Ala Ser Gln Ser Phe Cys
            885                 890                 895

Glu Ser Ser Ser Glu Thr Pro Phe His Phe Thr Leu Pro Lys Glu Gly
                900                 905                 910

Asp Ile Ile Pro Pro Leu Thr Gly Ala Thr Pro Pro Leu Ile Gly His
            915                 920                 925

Leu Lys Leu Glu Pro Lys Arg His Ser Thr Pro Ile Gly Ile Ser Asn
    930                 935                 940

Tyr Pro Glu Ser Thr Ile Ala Thr Ser Asp Val Met Ser Glu Ser Met
945                 950                 955                 960

Val Glu Thr His Asp Pro Ile Leu Gly Ser Gly Lys Gly Asp Ser Gly
                965                 970                 975

Ala Ala Pro Asp Val Asp Asp Lys Leu Cys Leu Arg Met Lys Leu Val
            980                 985                 990

Ser Pro Glu Thr Glu Ala Ser Glu Glu Ser Leu Gln Phe Asn Leu Glu
        995                 1000                1005

Lys Pro Ala Thr Gly Glu Arg Lys Asn Gly Ser Thr Ala Val Ala
    1010                1015                1020

Glu Ser Val Ala Ser Pro Gln Lys Thr Met Ser Val Leu Ser Cys
    1025                1030                1035

Ile Cys Glu Ala Arg Gln Glu Asn Glu Ala Arg Ser Glu Asp Pro
    1040                1045                1050

Pro Thr Thr Pro Ile Arg Gly Asn Leu Leu His Phe Pro Ser Ser
    1055                1060                1065

Gln Gly Glu Glu Glu Lys Glu Lys Leu Glu Gly Asp His Thr Ile
    1070                1075                1080

Arg Gln Ser Gln Gln Pro Met Lys Pro Ile Ser Pro Val Lys Asp
    1085                1090                1095

Pro Val Ser Pro Ala Ser Gln Lys Met Val Ile Gln Gly Pro Ser
    1100                1105                1110

Ser Pro Gln Gly Glu Ala Met Val Thr Asp Val Leu Glu Asp Gln
    1115                1120                1125

Lys Glu Gly Arg Ser Thr Asn Lys Glu Asn Pro Ser Lys Ala Leu
    1130                1135                1140

Ile Glu Arg Pro Ser Gln Asn Asn Ile Gly Ile Gln Thr Met Glu
    1145                1150                1155

Cys Ser Leu Arg Val Pro Glu Thr Val Ser Ala Ala Thr Gln Thr
    1160                1165                1170

Ile Lys Asn Val Cys Glu Gln Gly Thr Ser Thr Val Asp Gln Asn
    1175                1180                1185

Phe Gly Lys Gln Asp Ala Thr Val Gln Thr Glu Arg Gly Ser Gly
    1190                1195                1200

Glu Lys Pro Val Ser Ala Pro Gly Asp Asp Thr Glu Ser Leu His
    1205                1210                1215

Ser Gln Gly Glu Glu Glu Phe Asp Met Pro Gln Pro Pro His Gly
    1220                1225                1230

-continued

```
His Val Leu His Arg His Met Arg Thr Ile Arg Glu Val Arg Thr
         1235            1240                1245

Leu Val Thr Arg Val Ile Thr Asp Val Tyr Tyr Val Asp Gly Thr
         1250            1255                1260

Glu Val Glu Arg Lys Val Thr Glu Glu Thr Glu Pro Ile Val
         1265            1270                1275

Glu Cys Gln Glu Cys Glu Thr Glu Val Ser Pro Ser Gln Thr Gly
         1280            1285                1290

Gly Ser Ser Gly Asp Leu Gly Asp Ile Ser Ser Phe Ser Ser Lys
         1295            1300                1305

Ala Ser Ser Leu His Arg Thr Ser Ser Gly Thr Ser Leu Ser Ala
         1310            1315                1320

Met His Ser Ser Gly Ser Ser Gly Lys Gly Ala Gly Pro Leu Arg
         1325            1330                1335

Gly Lys Thr Ser Gly Thr Glu Pro Ala Asp Phe Ala Leu Pro Ser
         1340            1345                1350

Ser Arg Gly Gly Pro Gly Lys Leu Ser Pro Arg Lys Gly Val Ser
         1355            1360                1365

Gln Thr Gly Thr Pro Val Cys Glu Glu Asp Gly Asp Ala Gly Leu
         1370            1375                1380

Gly Ile Arg Gln Gly Gly Lys Ala Pro Val Thr Pro Arg Gly Arg
         1385            1390                1395

Gly Arg Arg Gly Arg Pro Pro Ser Arg Thr Thr Gly Thr Arg Glu
         1400            1405                1410

Thr Ala Val Pro Gly Pro Leu Gly Ile Glu Asp Ile Ser Pro Asn
         1415            1420                1425

Leu Ser Pro Asp Asp Lys Ser Phe Ser Arg Val Val Pro Arg Val
         1430            1435                1440

Pro Asp Ser Thr Arg Arg Thr Asp Val Gly Ala Gly Ala Leu Arg
         1445            1450                1455

Arg Ser Asp Ser Pro Glu Ile Pro Phe Gln Ala Ala Ala Gly Pro
         1460            1465                1470

Ser Asp Gly Leu Asp Ala Ser Ser Pro Gly Asn Ser Phe Val Gly
         1475            1480                1485

Leu Arg Val Val Ala Lys Trp Ser Ser Asn Gly Tyr Phe Tyr Ser
         1490            1495                1500

Gly Lys Ile Thr Arg Asp Val Gly Ala Gly Lys Tyr Lys Leu Leu
         1505            1510                1515

Phe Asp Asp Gly Tyr Glu Cys Asp Val Leu Gly Lys Asp Ile Leu
         1520            1525                1530

Leu Cys Asp Pro Ile Pro Leu Asp Thr Glu Val Thr Ala Leu Ser
         1535            1540                1545

Glu Asp Glu Tyr Phe Ser Ala Gly Val Val Lys Gly His Arg Lys
         1550            1555                1560

Glu Ser Gly Glu Leu Tyr Tyr Ser Ile Glu Lys Glu Gly Gln Arg
         1565            1570                1575

Lys Trp Tyr Lys Arg Met Ala Val Ile Leu Ser Leu Glu Gln Gly
         1580            1585                1590

Asn Arg Leu Arg Glu Gln Tyr Gly Leu Gly Pro Tyr Glu Ala Val
         1595            1600                1605

Thr Pro Leu Thr Lys Ala Ala Asp Ile Ser Leu Asp Asn Leu Val
         1610            1615                1620

Glu Gly Lys Arg Lys Arg Arg Ser Asn Val Ser Ser Pro Ala Thr
```

-continued

```
             1625                1630                1635
Pro Thr Ala Ser Ser Ser  Ser Thr Thr Pro  Thr Arg Lys Ile
    1640             1645              1650

Thr Glu Ser Pro Arg Ala  Ser Met Gly Val  Leu Ser Gly Lys Arg
    1655             1660              1665

Lys Leu Ile Thr Ser Glu  Glu Glu Arg Ser  Pro Ala Lys Arg Gly
    1670             1675              1680

Arg Lys Ser Ala Thr Val  Lys Pro Gly Ala  Val Gly Ala Gly Glu
    1685             1690              1695

Phe Val Ser Pro Cys Glu  Ser Gly Asp Asn  Thr Gly Glu Pro Ser
    1700             1705              1710

Ala Leu Glu Glu Gln Arg  Gly Pro Leu Pro  Leu Asn Lys Thr Leu
    1715             1720              1725

Phe Leu Gly Tyr Ala Phe  Leu Leu Thr Met  Ala Thr Thr Ser Asp
    1730             1735              1740

Lys Leu Ala Ser Arg Ser  Lys Leu Pro Asp  Gly Pro Thr Gly Ser
    1745             1750              1755

Ser Glu Glu Glu Glu Glu  Phe Leu Glu Ile  Pro Pro Phe Asn Lys
    1760             1765              1770

Gln Tyr Thr Glu Ser Gln  Leu Arg Ala Gly  Ala Gly Tyr Ile Leu
    1775             1780              1785

Glu Asp Phe Asn Glu Ala  Gln Cys Asn Thr  Ala Tyr Gln Cys Leu
    1790             1795              1800

Leu Ile Ala Asp Gln His  Cys Arg Thr Arg  Lys Tyr Phe Leu Cys
    1805             1810              1815

Leu Ala Ser Gly Ile Pro  Cys Val Ser His  Val Trp Val His Asp
    1820             1825              1830

Ser Cys His Ala Asn Gln  Leu Gln Asn Tyr  Arg Asn Tyr Leu Leu
    1835             1840              1845

Pro Ala Gly Tyr Ser Leu  Glu Glu Gln Arg  Ile Leu Asp Trp Gln
    1850             1855              1860

Pro Arg Glu Asn Pro Phe  Gln Asn Leu Lys  Val Leu Leu Val Ser
    1865             1870              1875

Asp Gln Gln Gln Asn Phe  Leu Glu Leu Trp  Ser Glu Ile Leu Met
    1880             1885              1890

Thr Gly Gly Ala Ala Ser  Val Lys Gln His  His Ser Ser Ala His
    1895             1900              1905

Asn Lys Asp Ile Ala Leu  Gly Val Phe Asp  Val Val Thr Asp
    1910             1915              1920

Pro Ser Cys Pro Ala Ser  Val Leu Lys Cys  Ala Glu Ala Leu Gln
    1925             1930              1935

Leu Pro Val Val Ser Gln  Glu Trp Val Ile  Gln Cys Leu Ile Val
    1940             1945              1950

Gly Glu Arg Ile Gly Phe  Lys Gln His Pro  Lys Tyr Lys His Asp
    1955             1960              1965

Tyr Val Ser His
    1970
```